(12) United States Patent
Yu et al.

(10) Patent No.: US 12,220,461 B2
(45) Date of Patent: Feb. 11, 2025

(54) POLYPEPTIDE-COUPLED SMALL MOLECULE COMPOUND AND ANTIVIRAL APPLICATION THEREOF

(71) Applicant: Guangzhou Medical University, Guangzhou (CN)

(72) Inventors: Xiyong Yu, Guangzhou (CN); Ao Shen, Guangzhou (CN); Hua Tao, Guangzhou (CN); Lixin Zhao, Guangzhou (CN); Nanshan Zhong, Guangzhou (CN); Qiulian Zhu, Guangzhou (CN)

(73) Assignee: Guangzhou Medical University, Guangzhou (CN)

( * ) Notice: Subject to any disclaimer, the term of this patent is extended or adjusted under 35 U.S.C. 154(b) by 0 days.

(21) Appl. No.: 18/667,958

(22) Filed: May 17, 2024

(65) Prior Publication Data
US 2024/0382604 A1    Nov. 21, 2024

(30) Foreign Application Priority Data

May 19, 2023    (CN) .......................... 202310567902.2

(51) Int. Cl.
*A61K 47/64*    (2017.01)
*A61P 31/14*    (2006.01)

(52) U.S. Cl.
CPC .............. *A61K 47/64* (2017.08); *A61P 31/14* (2018.01)

(58) Field of Classification Search
CPC ................................ A61K 47/64; A61P 31/14
See application file for complete search history.

(56) References Cited

U.S. PATENT DOCUMENTS

2007/0066800 A1* 3/2007 Sidhu ....................... A61P 25/00
                                                    435/254.2

FOREIGN PATENT DOCUMENTS

| CN | 113735937 A | 12/2021 |
| WO | WO-2022072975 A1 * | 4/2022 |

OTHER PUBLICATIONS

Anirudhan et al, "Targeting SARS-CoV-2 viral proteases as a therapeutic strategy to treat COVID-19," J. Med. Virol. 93:2722-2734 (2021) (Year: 2021).*
Liu et al, "Design and Evaluation of a Novel Peptide-Drug Conjugate Covalently Targeting SARS-CoV-2 Papain-like Protease," J. Med. Chem. 65:876-884 (Jan. 2022) (Year: 2022).*
Kiira Ratia et al., "A noncovalent class of papain-like protease/deubiquitinase inhibitors blocks SARS virus replication", Proceedings of the National Academy of Sciences, 2008, pp. 16119-16124, vol. 105, No. 42.
CNIPA, Notification of First Office Action for CN202310567902.2, Oct. 11, 2023.
Guangzhou Medical University (Applicant), Reply to Notification of First Office Action for CN202310567902.2, w/(allowed) replacement claims, Nov. 13, 2023.
CNIPA, Notification to grant patent right for invention in CN202310567902.2, Nov. 21, 2023.

* cited by examiner

*Primary Examiner* — Julie Ha
*Assistant Examiner* — Kristina M Hellman
(74) *Attorney, Agent, or Firm* — Hemisphere Law, PLLC; Zhigang Ma

(57) ABSTRACT

A polypeptide-coupled small molecule compound and its antiviral applications are provided. The polypeptide-coupled small molecule compound is obtained by linking a polypeptide with a sequence X'nLXGG and a small molecule compound capable of inhibiting activity of papain-like protease (PLpro) of coronavirus through a chemical bond. The polypeptide with the sequence X'nLXGG is a polypeptide with a sequence LXGG at its carboxyl terminal, X and X' are independently any amino acid, and n is an integer between 1-50. The structure of the small molecule compound capable of inhibiting the activity of PLpro contains an amino group or a hydroxyl group. The polypeptide-coupled small molecule compound can inhibit the PLpro of SARS-CoV-2 in a targeted manner, thereby inhibiting the polyprotein cleavage of coronavirus in the host, and achieving the purpose of inhibiting the replication of coronavirus in the host. It has the advantages of synergistic inhibition, low cytotoxicity and favorable solubility.

9 Claims, 12 Drawing Sheets

Specification includes a Sequence Listing.

POLYPEPTIDE-COUPLED SMALL MOLECULE COMPOUND AND ANTIVIRAL APPLICATION THEREOF

CROSS-REFERENCE TO RELATED APPLICATION

This application claims priority to Chinese patent application No. CN202310567902.2, filed to China National Intellectual Property Administration (CNIPA) on May 19, 2023, which is herein incorporated by reference in its entirety.

TECHNICAL FIELD

The disclosure relates to the technical field of medicines, and more particularly to a polypeptide-coupled small molecule compound and applications thereof.

STATEMENT REGARDING SEQUENCE LISTING

The sequence listing associated with this application is provided in text format in lieu of a paper copy and is hereby incorporated by reference into the specification. The name of the XML file containing the sequence listing is updated-24043TBYX-USP1-SL.xml. The XML file is 17,066 20,747 bytes; is created on Jul. 29, 2024; and is being submitted electronically via Patent Center.

BACKGROUND

Coronaviruses are a large class of viruses widely existing in nature, and belong to the family of positive-strand RNA viruses. At present, seven types of coronaviruses are known to infect humans, including human coronavirus 229E (HCoV-229E), HCoV-OC43, HCoV-NL63, HCoV-HKU1, severe acute respiratory syndrome-coronavirus (SARS-CoV, causing SARS) and Middle East respiratory syndrome-coronavirus (MERS-CoV, causing MERS). The seventh coronavirus recently discovered is known as the 2019 novel coronavirus (2019-nCoV, causing COVID-19), which has been designated as severe acute respiratory syndrome coronavirus 2 (SARS-CoV-2) by the International Committee on Taxonomy of Viruses (ICTV). COVID-19 is highly contagious and pathogenic, leading to a global epidemic. Although the world health organization (WHO) has announced that the COVID-19 epidemic no longer constitutes a public health emergency of international concern, at least 20 million people have died from SARS-CoV-2 since the onset of the COVID-19 epidemic. Coronaviruses have caused global public health crises such as SARS, MERS and COVID-19 in less than 20 years, posing serious threats to human health. In order to cope with the current epidemic situation in COVID-19 and other highly pathogenic coronaviruses that may appear at any time in the future, effective anti-coronavirus drugs are urgently needed. At present, the anti-SARS-CoV-2 drugs mainly include nucleoside analogue inhibitors targeting viral RNA-dependent RNA polymerase (RdRp) such as Remdesivir, Molnupiravir, VV116 and Azvudine, as well as polypeptide analogue inhibitors targeting viral 3C-like protease (3CLpro) such as Nirmatrelvir and Leritrelvir. These drugs inhibit the replication of SARS-CoV-2 by inhibiting RdRp or 3CLpro activity, thereby treating COVID-19. However, with the exception of Nirmatrelvir and Leritrelvir, all the aforementioned drugs are originally developed for human immunodeficiency virus (HIV) or other RNA viruses, resulting in low specificity for SARS-CoV-2 and unsatisfactory inhibitory effect. Moreover, the oral bioavailability of these drugs is low. In addition, SARS-CoV-2 mutates rapidly, making drug resistance easily occurred when using single-target drugs. Therefore, multi-target cooperative therapy is considered as the optimal strategy for the prevention and treatment of SARS-CoV-2.

In addition to the above two targets of anti-SARS-CoV-2 drugs, papain-like protease (PLpro) of SARS-CoV-2 is a new target with great potential. After SARS-CoV-2 infects the host, the virus gene first expresses two polyproteins, pp1a and pp1ab, which need to be cleaved by two proteases of SARS-CoV-2, the PLpro and the 3CLpro, into 16 non-structural proteins (Nsp1 to Nsp16) for viral replication to occur. Specifically, the PLpro releases the Nsp1 to the Nsp3 from the polyproteins by recognizing the conserved amino acid sequence LXGG. There are specific tetrapeptides LXGG between Nsp1 and Nsp2, Nsp2 and Nsp3, Nsp3 and Nsp4, and the cleavage by the PLpro occurs after the second G. The PLpro can also catalyze the removal of ubiquitin and interferon-stimulated gene 15 (ISG15) linked to the host protein to escape the host's antiviral innate immune response. The PLpro is rarely mutated in SARS-CoV-2 and is highly conserved. In addition, recognition and cleavage sites of viral PLpro and mammalian PLpro analogues (also known as cathepsins) are different. Moreover, given the high amino acid sequence homology and shared functionality with the other six coronaviruses that can infect humans, studies have confirmed that the small molecule inhibitors previously screened against the PLpro of other coronaviruses before the COVID-19 outbreak also have a good inhibitory effect on SARS-CoV-2 PLpro.

At present, reported small molecule compounds with inhibitory effects on SARS-CoV-2 PLpro include GRL0617, Maprotiline, Reserpine, Levothyroxine, Loperamide, Manidipine, Proanthocyanidin, Disulfiram, and 6-thioguanine (6-TG). Notably, GRL0617 is a small molecule inhibitor against SARS-CoV PLpro initially identified by Kiira Ratia et al. in 2008 (Kiira Ratia et al., "A noncovalent class of papain-like protease/deubiquitinase inhibitors blocks SARS virus replication", Proceedings of the National Academy of Sciences, 2008, pp. 16119-16124, Vol. 105, No. 42), and studies have shown that GRL0617 is also the most potent inhibitor of SARS-CoV-2 PLpro to date. However, the clinical application of GRL0617 is hindered by its high cytotoxicity and poor solubility. Besides GRL0617, most of the other small molecule compounds are approved drugs with specific targets and indications, they are not specific PLpro inhibitors. Consequently, their inhibitory effects on the SARS-CoV-2 PLpro are not as good as GRL0617.

SUMMARY

In view of this, the disclosure provides a kind of polypeptide-coupled small molecule compound, which is obtained by chemically linking a polypeptide containing the amino acid sequence LXGG specifically recognized and cleaved by coronavirus PLpro with a small molecule compound capable of inhibiting PLpro activity. The polypeptide-coupled small molecule compound can target and inhibit PLpro thereby inhibit polyprotein cleavage of the coronavirus in the host, thereby curbing viral replication, ultimately achieving the purpose of anti-coronavirus. In addition, the polypeptide-coupled small molecule compound operates synergistically to inhibit PLpro activity, leveraging both the specific substrate polypeptide of PLpro and the small molecule compound released post-cleavage of the polypeptide. This dual mechanism enhances the inhibition of PLpro, elevating the compound's antiviral efficacy. The polypeptide-coupled small molecule compound has low cytotoxicity and favorable solubility, which is beneficial to its antiviral application.

The disclosure includes the following technical solutions.

Specifically, a polypeptide-coupled small molecule compound is obtained by linking a polypeptide with a sequence X'nLXGG and a small molecule compound through a chemical bond.

The polypeptide with the sequence X'nLXGG is a polypeptide with a sequence LXGG at its carboxyl terminal, X and X' are each independently any amino acid, n represents the number of amino acids, and n is an integer between 1-50. In addition, L represents leucine and G represents glycine.

The small molecule compound is capable of inhibiting activity of PLpro of a coronavirus, and a structure of the small molecule compound contains an amino group or a hydroxyl group.

In some embodiments, X in the polypeptide is selected from the following amino acids: arginine (R), arginine (N), and lysine (K).

In some embodiments, n is the integer between 1-30.

In some embodiments, n is the integer between 1-10.

In some embodiments, n is the integer selected from the group consisting of: 1, 2, 3, 4, and 5.

In some embodiments, the amino acid sequence of the polypeptide is SRLRGG (SEQ ID NO: 1). S represents serine.

In some embodiments, the small molecule compound that can inhibit the activity of PLpro is one selected from the group consisting of GRL0617, 6-thioguanine, levothyroxine, loperamide, and proanthocyanidin. The structural formulas are as follows:

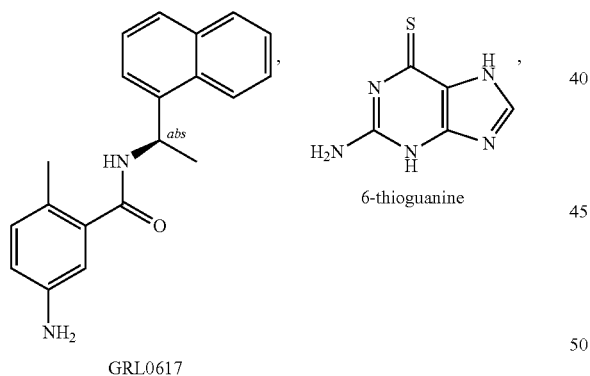

GRL0617

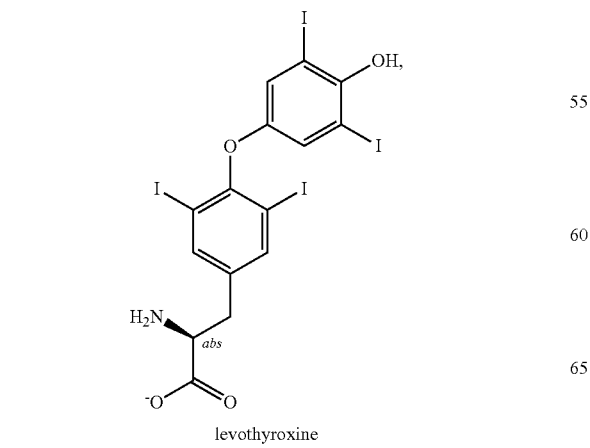

levothyroxine

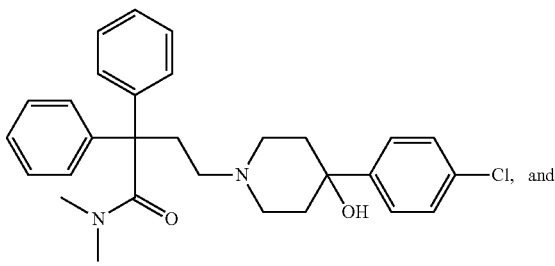

loperamide

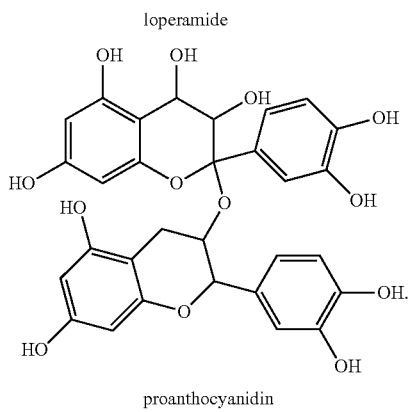

proanthocyanidin

In some embodiments, a carboxyl group at a C-terminal of the polypeptide and the small molecule compound are connected by an amide bond or an ester bond.

In some embodiments, the polypeptide-coupled small molecule compound has the following structural formula:

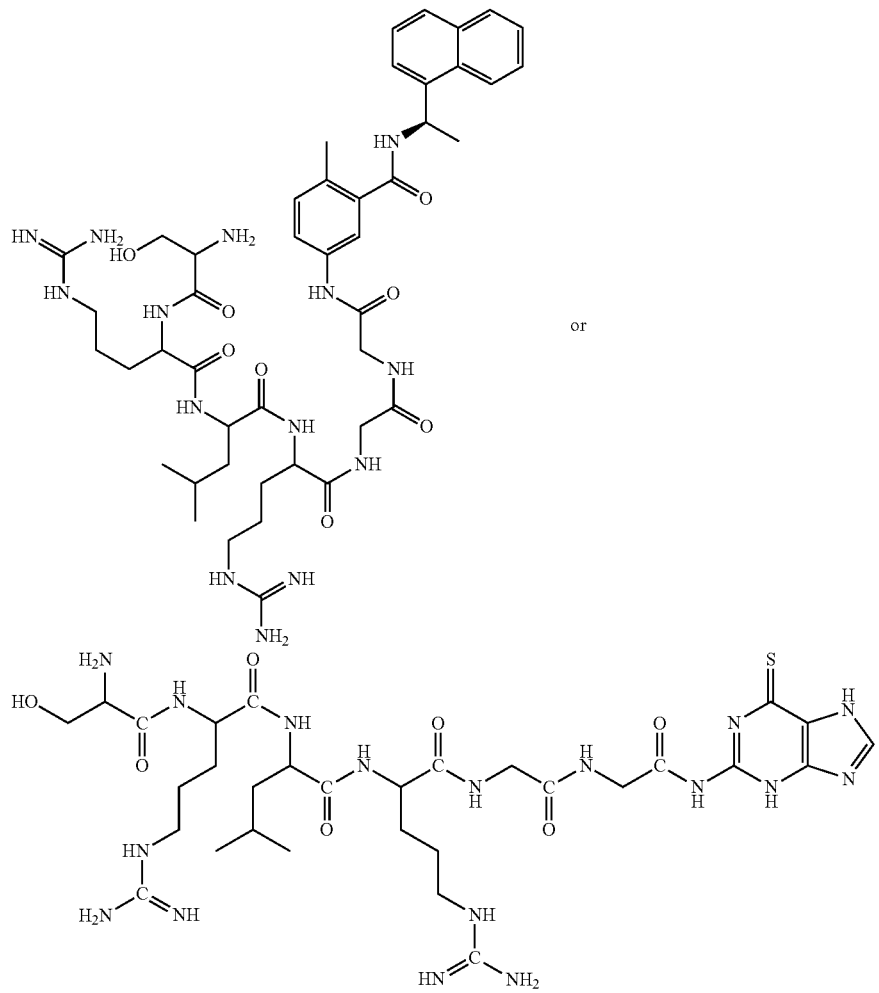

The disclosure also provides applications of the polypeptide-coupled small molecule compound, including the following technical solutions.

Specifically, an application of the polypeptide-coupled small molecule compound in preparing an inhibitor of the PLpro of the coronavirus is provided.

An application of the polypeptide-coupled small molecule compound in preparing a drug against the coronavirus is provided.

An application of the polypeptide-coupled small molecule compound in preparing a drug for at least one of preventing and treating a disease caused by the coronavirus is provided.

In some embodiments, the coronavirus is SARS-CoV-2.

The disclosure also provides an anti-coronavirus drug, which includes the following technical solution.

Specifically, an anti-coronavirus drug is prepared from an active ingredient and a pharmaceutically acceptable excipient, and the active ingredient includes the polypeptide-coupled small molecule compound.

The disclosure designs and synthesizes a polypeptide-based inhibitor, which is connected by chemically linking the polypeptide containing the amino acid sequence LXGG specifically recognized and cleaved by the coronavirus PLpro with the small molecule compound capable of inhibiting PLpro activity, thus forming a novel peptide-drug conjugate. The inhibitor can inhibit the SARS-CoV-2 PLpro to thereby inhibit the polyprotein cleavage of the coronavirus in the host, thereby curbing viral replication, ultimately achieving the purpose of anti-coronavirus.

The PLpro is an indispensable and highly conserved protease for SARS-CoV-2 to replicate in the host, and inhibition of its activity can inhibit the replication of SARS-CoV-2. The PLpro is highly homologous in coronavirus, and its inhibitor is also a broad-spectrum coronavirus inhibitor, which is a promising anti-coronavirus target. Compared with the existing PLpro inhibitors, the PLpro polypeptide-based inhibitor (the polypeptide-coupled small molecule compound) designed and synthesized by the disclosure has four advantages as follows. (1) The polypeptide, linked with a small molecule compound, serves as the specific substrate of the PLpro, which can competitively inhibit the activity of the PLpro. (2) After the PLpro cleaves the polypeptide-coupled small molecule compound, the released small molecule compound further inhibits the activity of the PLpro, augmenting the inhibitory effect through synergistic inhibition of both the specific substrate polypeptide and the small molecule compound. (3) The drug selectively releases the small molecule compound only in the presence of PLpro, thereby avoiding the cytotoxicity associated with standalone use of the small molecule compound and endows the drug with targeting to the PLpro. (4) By adjusting the amino acid sequence, properties such as hydrophobicity, ionization can be easily modulated to optimize pharmacokinetics and improve the bioavailability of the drug. For example, the octanol-water partition coefficient log P of the drug can be set in a suitable range, which is beneficial to the dissolution and absorption of the drug in vivo.

Therefore, the polypeptide-coupled small molecule compound designed and synthesized by the disclosure can strongly inhibit the activity of the PLpro, for example, the inhibitory activity of RG-17 in the embodiment is superior to that of existing small molecule inhibitors such as GRL0617. In addition, the polypeptide-coupled small molecule compound of the disclosure can significantly reduce cytotoxicity, for example, RG-17 and RG-6 formed by coupling the small molecule compound with the polypeptide in the embodiments have significantly lower cytotoxicity than that of single small molecule compound. Compared with the reported PLpro small molecule inhibitors, the polypeptide-based inhibitor of the disclosure has the advantages of PLpro targeting, low cytotoxicity, and easy pharmacokinetic optimization, and is a very promising PLpro inhibitor and an antiviral drug. It can strongly inhibit the activity of the PLpro of coronavirus and significantly inhibit the replication of coronavirus, so it can be used as an anti-SARS-CoV-2 drug.

DETAILED DESCRIPTION OF EMBODIMENTS

Figure 1:
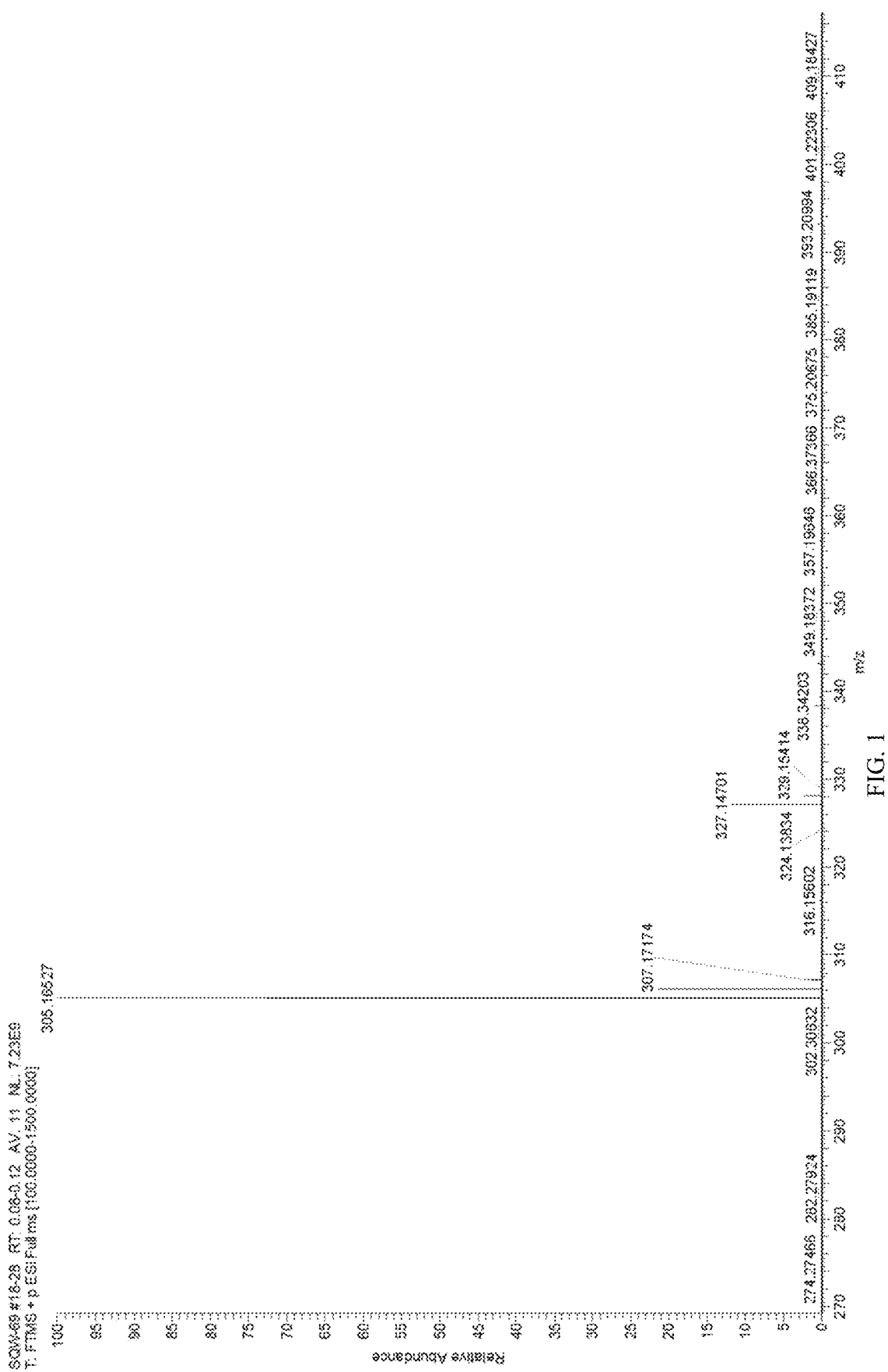
FIG. 1 illustrates a mass spectrum identification diagram of GRL0617.

In the following embodiments of the disclosure, experimental methods without specific conditions are usually in accordance with conventional conditions or conditions suggested by the manufacturer. Various common chemical reagents used in the embodiments are all commercially available products.

Unless otherwise defined, all technical and scientific terms used in this disclosure have the same meaning as commonly understood by those skilled in the related art of the disclosure. The terms used in the specification of the disclosure are only for the purpose of describing specific embodiments and are not used to limit the disclosure.

The terms "including" and "having" and any variations thereof in the disclosure are intended to cover non-exclusive inclusion. For example, a process, a method, a device, a product, or an equipment that includes a series of steps is not limited to the listed steps or modules, but optionally includes steps that are not listed, or optionally includes other steps inherent to the process, the method, the product, or the equipment.

In the disclosure, "multiple" refers to two or more. "and/or", which describes the relationship of related objects, means that there can be three kinds of relationships, for example, A and/or B, which can mean that A exists alone, A and B exist together, and B exists alone. The character "/" generally indicates an "or" relationship between objects associated before and after.

The disclosure will be further elaborated with specific embodiments. It should be understood that these embodiments are only used to illustrate the disclosure and are not used to limit the scope of the disclosure.

Embodiment 1 Synthesis of Small Molecule Inhibitor GRL0617 of PLpro

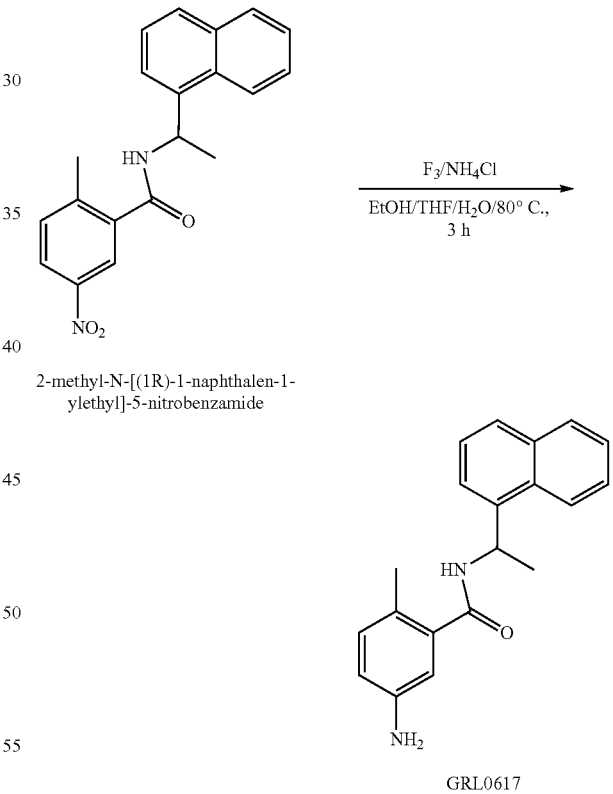

2-methyl-N-[(1R)-1-naphthalen-1-ylethyl]-5-nitrobenzamide

GRL0617

1.1 2-methyl-N-[(1R)-1-naphthalen-1-ylethyl]-5-nitrobenzamide (30 millimoles per liter abbreviated as mM, 1.0 equivalent abbreviated as equiv) is weighed in a 5 milliliters (mL) reaction bottle, and tetrahydrofuran abbreviated as THF (0.1 moles per liter abbreviated as M) and ethanol abbreviated as EtOH (0.1 M) are added and dissolved, so as to obtain a mixed solution.

1.2 Ammonium chloride abbreviated as $NH_4Cl$ (150 mM, 5.0 equiv) is added and dissolved in water to obtain a $NH_4Cl$ solution, then the NH$_4$Cl solution is added into the mixed solution of the step 1.1. Then, the reaction bottle is put into an oil bath pot at 80° C., the weighed iron powder (120 mM, 4.0 equiv) is added into the reaction bottle under stirring. The reflux reaction is performed for 3 hours (h), and the end point of the reaction is monitored by thin-layer chromatography (TLC).

1.3 After the reaction, diatomite and silica gel powder are used as separation fillers in a sintered funnel, and ethyl acetate (EA) is used for rinsing and vacuum filtration to remove the iron powder and other impurities. The product GRL0617 is isolated and purified by TLC (eluent: petroleum ether abbreviated as PE/EA=2/1) after removing water and solvent by extraction and rotary evaporation.

Figure 2:
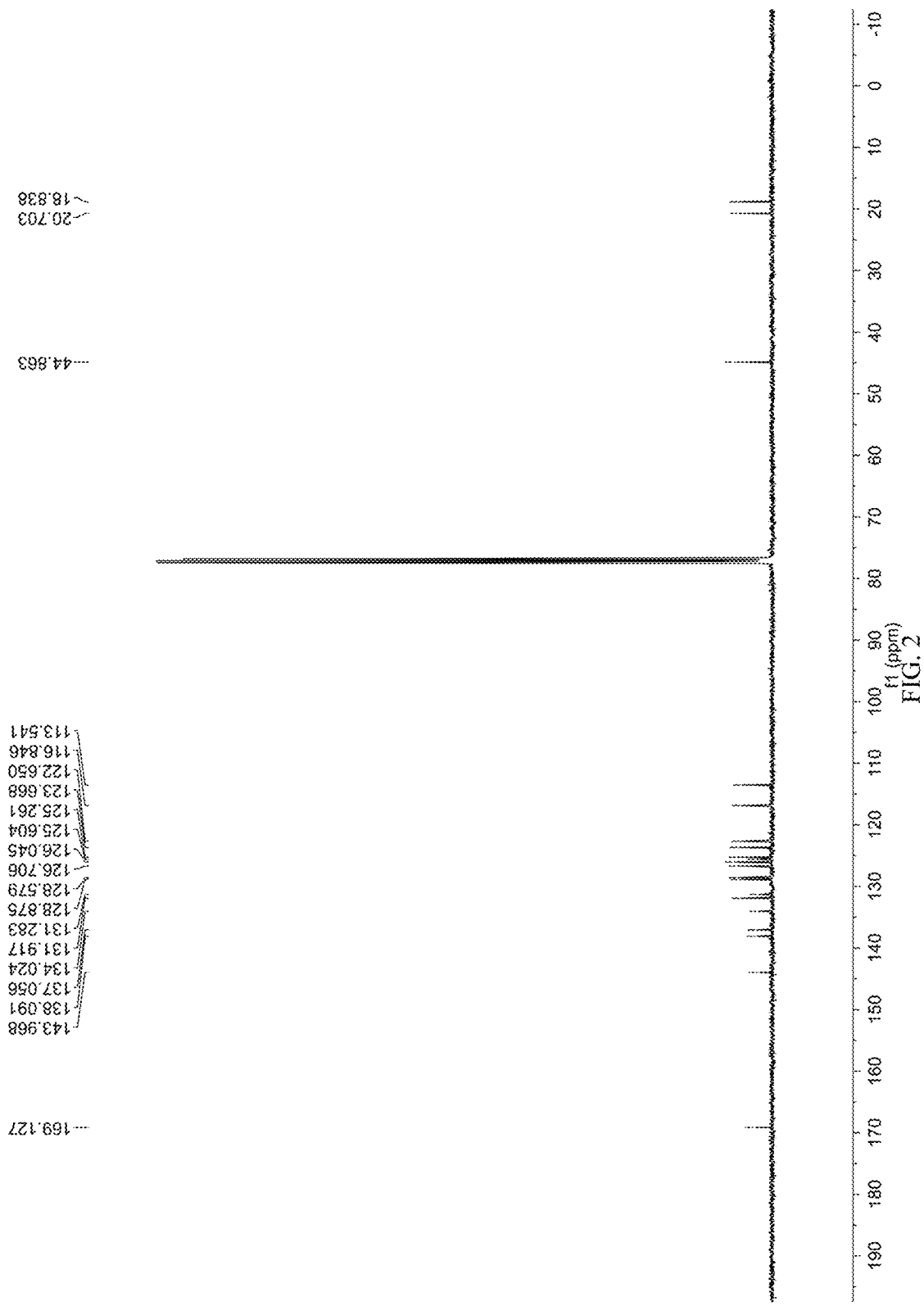
FIG. 2 illustrates a carbon spectrum identification diagram of the GRL0617.
Figure 3:
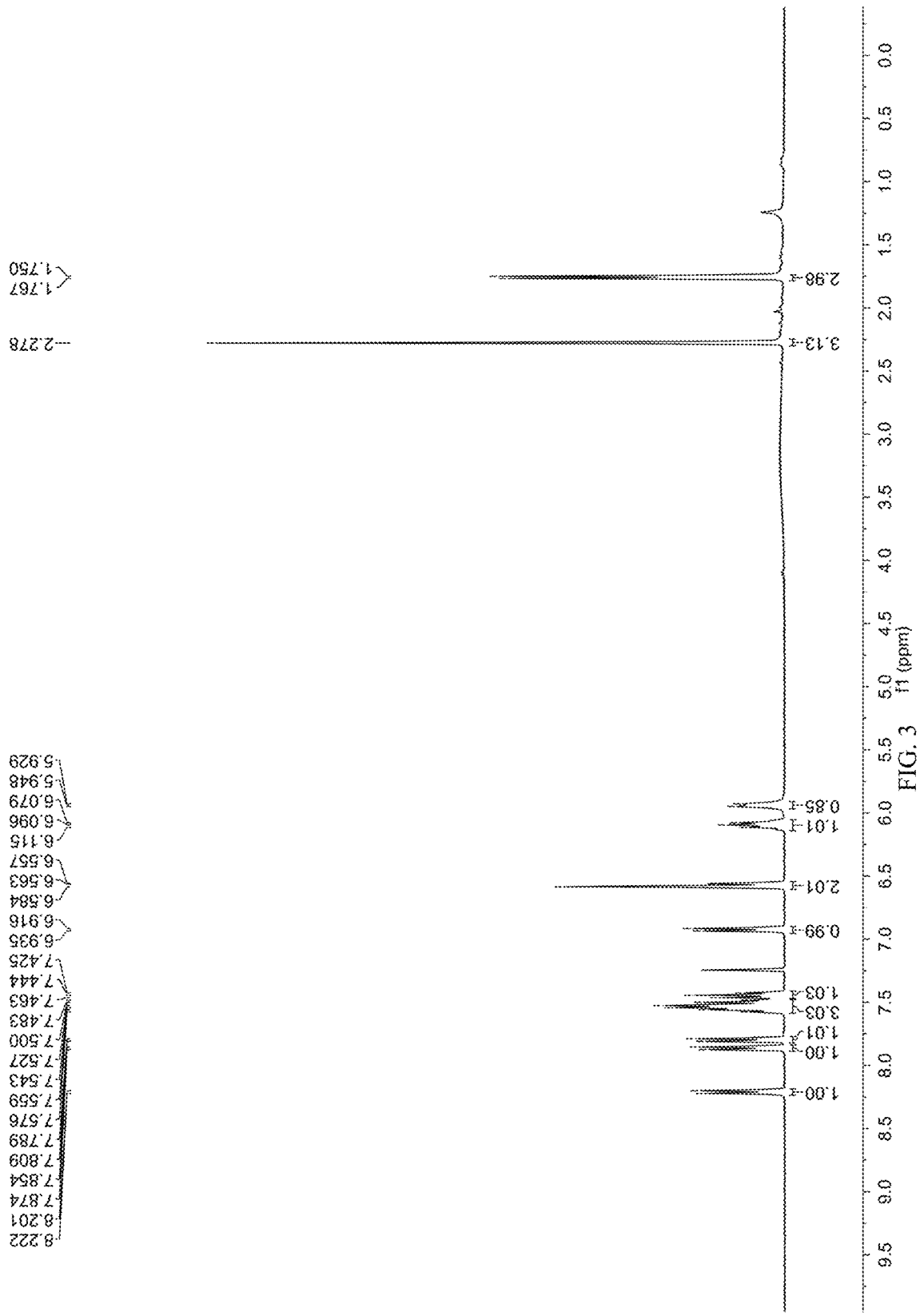
FIG. 3 illustrates a hydrogen spectrum identification diagram of the GRL0617.

1.4 The product is identified by means of carbon spectrum, hydrogen spectrum and mass spectrometry. The results show that the product is GRL0617, which has no other impurities and can be used for the next synthesis. (FIG. 1-FIG. 3) $^1$H NMR (400 MHZ, CDCl3) δ 8.22 (d, J=8.5 Hz, 1H), 7.88 (d, J=8.1 Hz, 1H), 7.81 (d, J=8.1 Hz, 1H), 7.59-7.49 (m, 3H), 7.46 (t, J=7.8 Hz, 1H), 6.94 (d, J=7.8 Hz, 1H), 6.59 (d, J=9.4 Hz, 2H), 6.10 (q, J=6.8, 6.1 Hz, 1H), 5.96 (d, J=8.4 Hz, 1H), 2.29 (s, 3H), 1.77 (d, J=6.6 Hz, 3H). $^{13}$C NMR (101 MHZ, CDCl3) δ 169.1, 144.0, 138.1, 137.1, 134.0, 131.9, 131.3, 128.9, 128.6, 126.7, 126.1, 125.6, 125.3, 123.7, 122.7, 116.9, 113.6, 44.9, 20.7, 18.8. HR-MS (ESI) m/z calcd for C20H21N2O [M+H]+305.1649, found 305.1653.

Embodiment 2 Synthesis of Polypeptide SRLRGG (SEQ ID NO: 1)

Polypeptide containing conserved sequence of LXGG is synthesized by solid-phase synthesis. In this embodiment, the hexapeptide SRLRGG (SEQ ID NO: 1) is taken as an example.

2.1 Treatment of solvents

Dimethyl fumarate (DMF) and methanol are soaked in a molecular sieve with G3 holes overnight to remove impurities and water before use.

2.2 Full swelling of resin 2.0 grams (g) of blank dichloride resin (also referred to as unloaded dichloride resin) are added into a clean and dry reaction tube, 15 mL DMF is added into the reaction tube, and activated at room temperature for about 30 minutes (min).

2.3 Connection of the first amino acid at the C-terminal

At room temperature, the solvents in the previous step are filtered off through a sintered funnel, and 1 millimole (mmol) of 5 times molar excess of the first amino acid 2-(9H-fluoren-9-ylmethoxycarbonylamino) acetic acid (Fmoc-Gly-OH) at the C-terminal, 5 times molar excess of 4-dimethylaminopyridine (DMAP), 5 times molar excess of dicyclohexylcarbodiimide (DIC) and DMF as a solvent are added to react for 3 h at room temperature. After the reaction, DMF is used for washing for 4-6 times, 5-6 mL each time. Then, a proper amount of pyridine and acetic anhydride in the volume ratio of 1:1 is added, and reacted for 30 min. After the reaction, DMF is used for washing for 4-6 times, 5-6 mL each time (the function is to block the active sites on the unreacted unloaded resin).

2.4 Removal of Fmoc protecting group

The solvent in the previous step is removed by suction filtration, 10 mL of DMF solution containing 20% piperidine is added into the resin. The solution is filtered out after stirring with nitrogen (N$_2$) for 10 min. Then, 10 mL of DMF solution containing 20% piperidine is added, and the solution is filtered after stirring with N$_2$ for 5 min. After repeating this operation twice, the solution is washed with DMF for 4 times and methanol for 2 times, 5-6 mL each time.

2.5 Removal effect of ninhydrin detection

A small amount of resin is taken out and washed with methanol for three times. One drop of each of ninhydrin, potassium cyanide (KCN) and phenol solutions are added, heated at 105° C.-110° C. for 5 min. When it is turned to be dark blue, indicating that it is a positive reaction, which means that the Fmoc protecting group is complete removed and the next reaction can be carried out. If it is colorless, it means that the protecting group has not been completely removed, and the above deprotection operation needs to be repeated.

2.6 Connection of the second amino acid and removal of Fmoc protecting group.

3 times molar excess of the second amino acid at C-terminal, 3 times molar excess of O-Benzotriazole-N,N,N',N'-tetramethyl-uronium-hexafluorophosphate (HBTU) and 3 times molar excess of 1-Hydroxybenzotriazole (HOBT) are weighed and added into a reaction tube, a proper amount of DMF solution is added to completely dissolve them, then 10 times molar excess of pure N,N-Diisopropylethylamine (DIEA) is added, reacted at room temperature for 40 min, and washed with DMF for 4-6 times, with 5-6 mL each time. A small amount of resin is taken and detected by ninhydrin detection reagent, and it is colorless. Then, 10 mL of DMF solution containing 20% piperidine is added to remove the Fmoc protecting group twice, for 10 min and 5 min respectively, and then washed with DMF for 4 times and methanol for 2 times, with 5-6 mL each time. A small amount of resin is taken and detected with ninhydrin detection reagent. When it is blue, the next reaction can be carried out.

2.7 By analogy, the step 2.6 is repeated until the last amino acid at the N-terminal is synthesized, the Fmoc protecting group is removed, NH$_2$ blue is detected with ninhydrin, and 2 times equivalent of carbonic anhydride di-tert-butyl ester (abbreviated as DIBOC or (Boc)2O) and DMF as solvents are added to react for 2 h at room temperature. After draining, the resin is washed twice with methanol, dichloromethane and DMF in turn, and the color of ninhydrin is colorless, which proves that the Boc connection is completed. Then, the resin is drained again.

2.8 Resin shedding and polypeptide separation

Finally, a trifluoroacetic acid (TFA) cutting solution (1% TFA: 2% triisopropylsilane abbreviated as TIS: 2% 1,2-ethanedithiol abbreviated as EDT: 95% H$_2$O) is used, fully protection and cutting are performed for twice, with 10 min each time, the cutting solution is collected for twice, with 10 min each time, and freeze-dried to obtain the crude fully protected polypeptide Boc-Ser(Tbu)-Arg (pbf)-Leu-Arg (pbf)-Gly-Gly-COOH (i.e., Boc-S(Tbu)R(pbf)LR(pbf)GG i.e., SEQ ID NO: 5).

Embodiment 3 Polypeptide SRLRGG (SEQ ID NO: 1) and GRL0617 are Linked to Obtain Peptide-Drug Conjugate RG-17

The crude fully protected polypeptide obtained in the embodiment 2 is dissolved in 15 mL of anhydrous pyridine, and the temperature is reduced to −15° C. 1 mL phosphorus oxychloride (POCl$_3$) solution to the solution is added, the anhydrous dichloromethane solution (1.5 equiv GRL0617) dissolved with GRL0617 is gradually added dropwise at −15° C., reacted for 2 h, and a crude product is obtained after spin-drying. A cutting solution (95% TFA, 2% TIS; 2%

Figure 4:
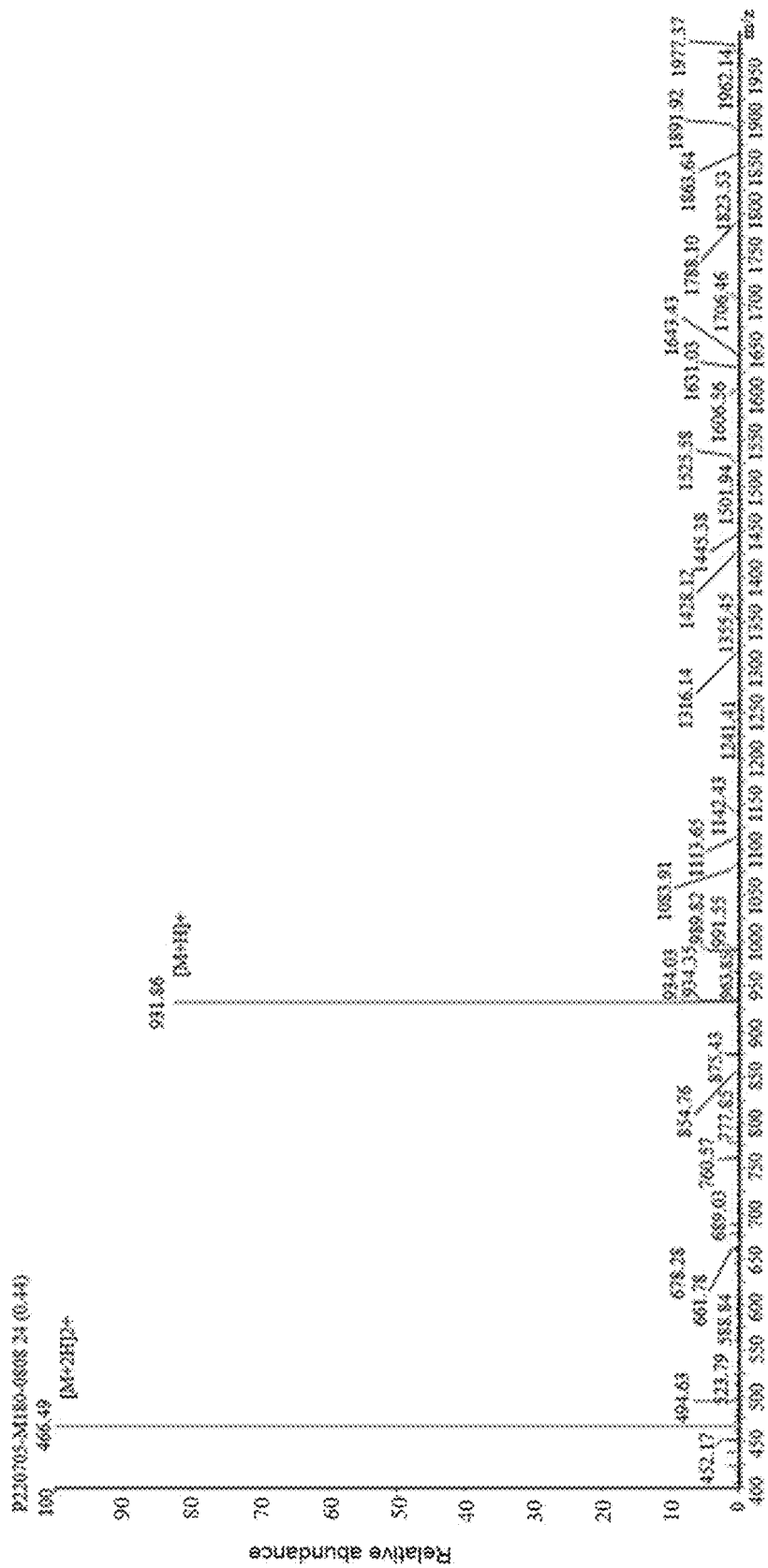
FIG. 4 illustrates a mass spectrum identification diagram of RG-17.
Figure 5:
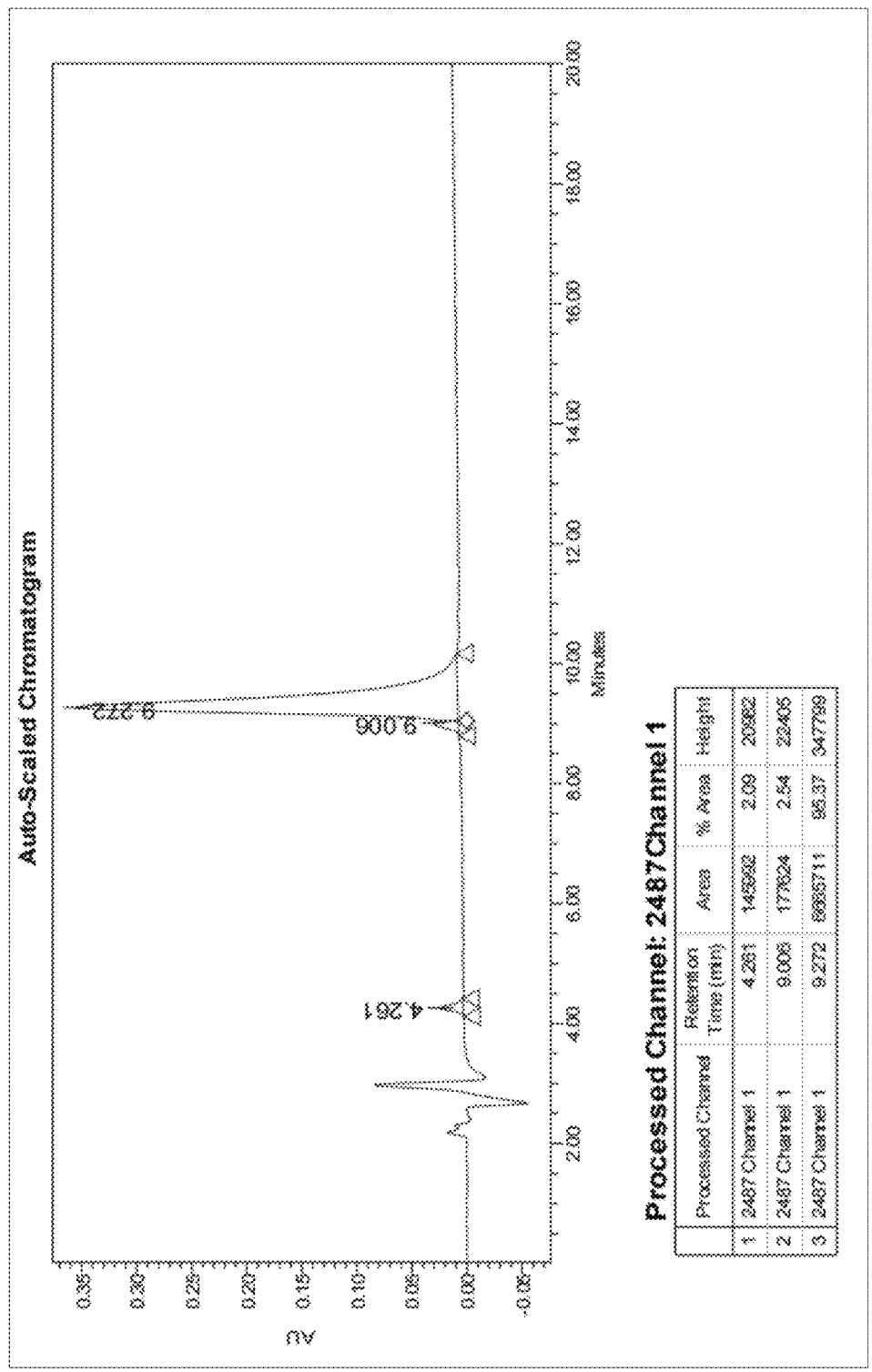
FIG. 5 illustrates a high-performance liquid chromatography (HPLC) identification diagram of the RG-17.

EDT; 2% hydrogen abbreviated as H$_2$) for 2 h, and a target product is obtained. It is confirmed by mass spectrometry (FIG. 4) and HPLC (FIG. 5) that the peptide-drug conjugate (also referred to as polypeptide coupled drug) RG-17 formed by connecting the polypeptide SRLRGG (SEQ ID NO: 1) and the GRL0615 is successfully obtained. Its purity is more than or equal to 95%, and its structural formula is as follows:

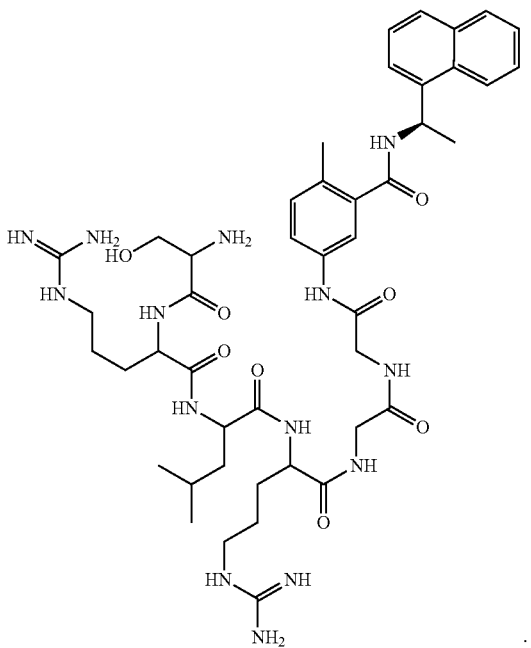 [SMILES: Cc1ccc(NC(=O)CNC(=O)CNC(=O)C(CCCNC(=N)N)NC(=O)C(CC(C)C)NC(=O)C(CCCNC(=N)N)NC(=O)C(N)CO)cc1C(=O)N[C@H](C)c1cccc2ccccc12]

Embodiment 4 Comparison of Physicochemical Properties Between RG-17 and GRL0617

The dissolution, absorption, distribution and transport of drugs in the body are all related to the water solubility and fat solubility of the drugs, that is, to the octanol-water partition coefficient (log P). The physicochemical properties of RG-17 and GRL0617 are evaluated by using the online website SwissADME. The results show that the log P of GRL0617 is 4.03, while that of RG-17 is 1.38. Compared with GRL0617, RG-17 has better water solubility and permeability of lipid bilayer, so its absorption effect in vivo is better.

Embodiment 5 Test of the Inhibitory Effect of RG-17 on PLpro In Vitro

The inhibitory effect (half maximal inhibitory concentration abbreviated as IC50) of RG-17 and GRL0617 on the activity of PLpro is tested by in vitro enzyme assay. The experimental principle is that PLpro can hydrolyze substrate RLRGG-AMC (SEQ ID NO: 6) to generate 7-amino-4-methylcoumarin (AMC), and the activity of PLpro can be calculated by detecting the fluorescence intensity of free AMC at 380 nanometers (nm) excitation wavelength and 460 nm emission wavelength. After the inhibitor is added, the fluorescence intensity of AMC is decreased. After a series of concentrations of inhibitors are added to the reaction system, the IC50 of the inhibitors is calculated by Prism software according to the change of the activity of PLpro. The specific experimental steps are as follows.

5.1 A reaction buffer is prepared according to the formula: dithiothreitol (DTT) 10 mM, tris(hydroxymethyl)aminomethane (Tris) 20 mM, sodium chloride (NaCl) 150 mM, and 2% dimethyl sulfoxide (DMSO).

5.2 Preparation of substrate: the substrate RLRGG-AMC (SEQ ID NO: 6) is diluted with the reaction buffer to a final concentration of 100 µM. Specifically, 198 microliters (µL) of the reaction buffer are taken and added with 2 µL of 10 mM substrate, and diluted to 100 µM, and mixed well.

5.3 Preparation of PLpro: the PLpro is diluted with the reaction buffer to 12.5 nanograms per microliter (ng/µL). 90 µL of the reaction buffer is taken and added with 10 µL of 125 ng/µL PLPro, and diluted to 12.5 ng/µL, and mixed well.

5.4 In the experimental group, 10 µL of 12.5 ng/uL PLpro is incubated with RG-17, GRL0617 or the polypeptide SRLRGG (SEQ ID NO: 1) with different concentrations at 37° C. for 10 min, and the final concentrations are 100 µM, 50 µM, 25 µM, 12.5 µM, 6.25 µM, 3.125 µM, 1.5625 µM, 0.7812 µM, 0.3906 µM, 0.1953 µM, 0.0976 µm, 0.0488 µm, 0.0244 µM respectively. The control group only used 10 µL of 12.5 ng/µL PLpro.

5.5 The prepared 100 µM substrate is quickly added into the above system, and a microplate reader is used to continuously read for 15 min under the incubation condition of 37° C., with each cycle interval of 30 seconds(s), in which the excitation wavelength is set to 380 nm and the emission wavelength is set to 460 nm.

5.6 Calculation of inhibition rate: the time min is taken as the X axis, the fluorescence value relative fluorescence unit (RFU) is taken as the Y axis, and the linear region fitting is taken to obtain the RFU/min as the enzyme activity, and then the inhibition rates of different concentrations of RG-17 or GRL0617 on PLpro are calculated according to the enzyme activities of the experimental group and the control group. The formula is as follows: inhibition rate=(1-enzyme activity of the experimental group/enzyme activity of the control group)×100%.

5.7 Calculation of IC50: using GraphPad Prism software, with X as drug concentration and Y as enzyme inhibition, IC50 is analyzed and calculated.

Figure 6A:
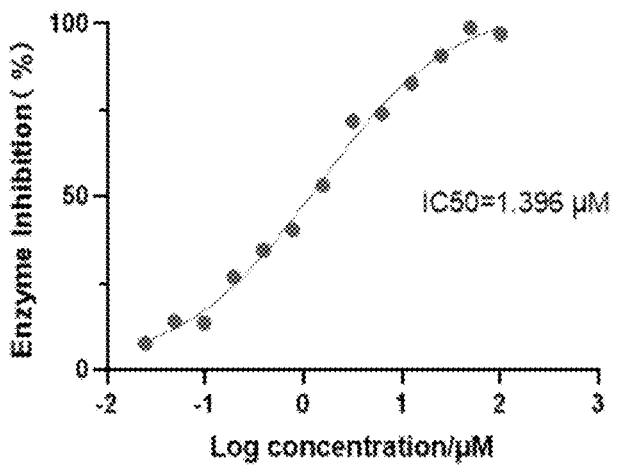
FIGS. 6A-6C illustrate comparison of inhibitory effects of the RG-17 and the GRL0617 on PLpro in vitro.
Figure 6B:
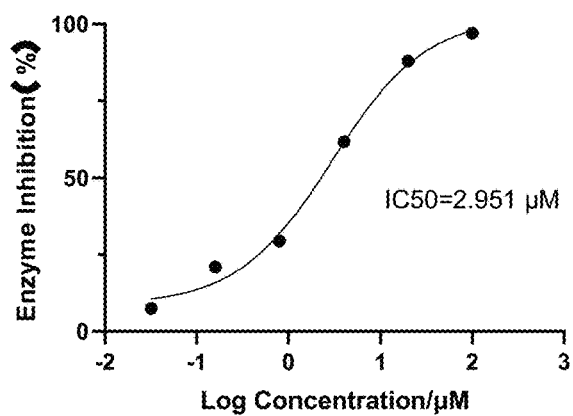
Figure 6C:
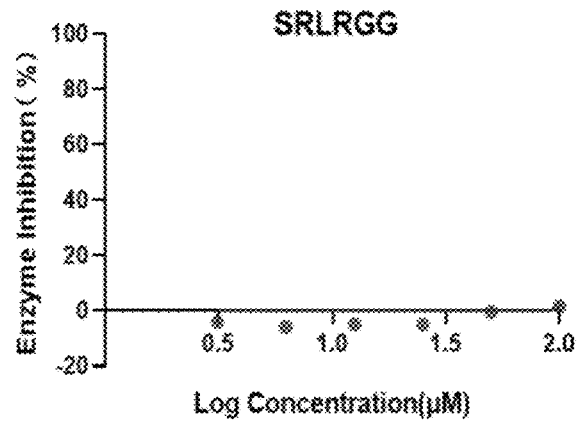
Figure 7A:
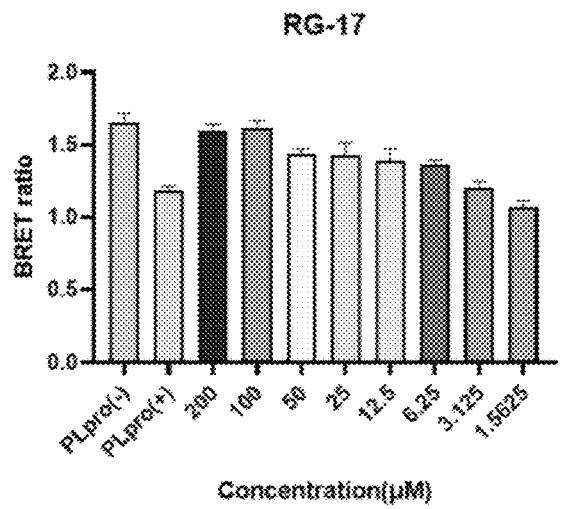
FIGS. 7A-7D illustrate comparison of inhibitory effects of the RG-17 and the GRL0617 on PLpro in vivo.
Figure 7B:
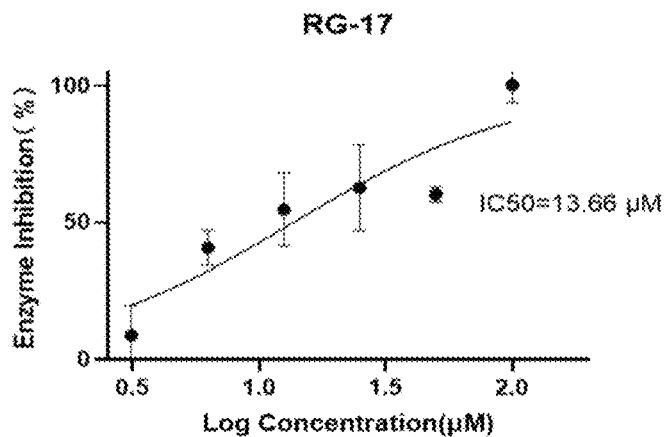
Figure 7C:
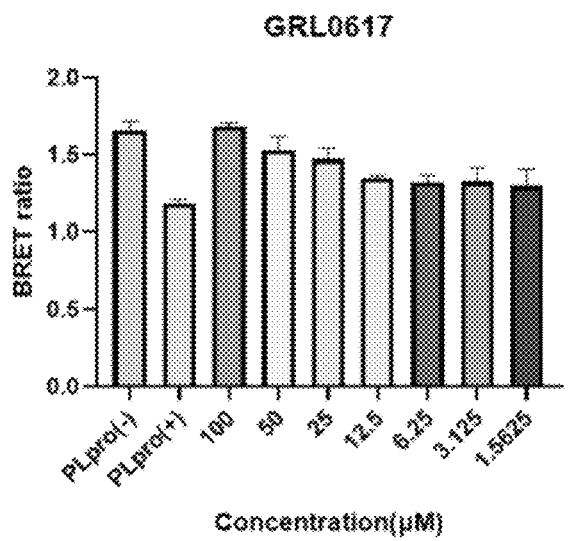
Figure 7D:
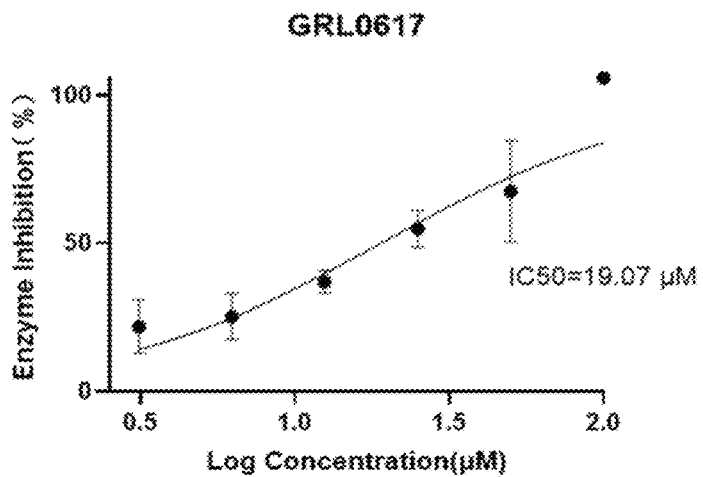

The results of in vitro enzyme assay shows that the IC50 of RG-17 is 1.396 µM, while that of GRL0617 as control is 2.951 µM, so the inhibitory effect of RG-17 on PLpro in vitro is better than that of GRL0617. However, the single polypeptide SRLRGG (SEQ ID NO: 1) has no inhibitory effect on PLpro due to the lack of chemical bonds at the C-terminal for PLpro digestion (FIGS. 6A-6C).

Embodiment 6 Test of the Inhibitory Effect of RG-17 on PLpro In Vivo

According to the bioluminescence resonance energy transfer (BRET) technology, the in vivo enzyme activity detection system of PLpro is constructed, and the inhibitory effect (IC50) of RG-17 and GRL0617 on the in vivo activity of PLpro is tested.

The experimental principle is as follows. The reporter plasmid (pEYFP-linker-Rluc, its gene sequence is SEQ ID NO: 2) carries a polycistron that simultaneously expresses yellow fluorescent protein, enhanced yellow fluorescent protein (EYFP), and luciferase, Renilla luciferase (Rluc), and the EYFP and Rluc are connected by a polypeptide (ITSRLRGGFRK i.e., SEQ ID NO: 3) that can be recognized and cleaved by PLpro. When the reporter plasmid is expressed in the cell and the fluorescein coelenterazine is added, the Rluc will hydrolyze the substrate coelenterazine to emit light. When the Rluc and the EYFP are connected by the polypeptide so that the distance is less than 10 nm, the luminescence of the Rluc can stimulate the EYFP to emit light, resulting in BRET effect. If the cell express PLpro protein (pcDNA3.1-PLpro, its gene sequence is SEQ ID NO: 4) at the same time, PLpro will cleave the connecting peptide to separate the Rluc from the EYFP, and the luminescence of EYFP will be weakened, resulting in the decrease of BRET ratio. However, when the PLpro inhibitor is added, the activity of PLpro is inhibited, the efficiency of cleaving the connecting peptide is decreased, the luminescence of EYFP will be enhanced, and the BRET ratio will be increased. After a series of concentrations of inhibitors are added to the reaction system, the IC50 of the inhibitors is calculated by Prism software according to the change of the activity of PLpro. The specific experimental steps are as follows.

6.1 Plating: 293T cells in logarithmic growth phase are inoculated into a 12-well plate (500 µL/well), and the number of cells in each well is set to $1\times10^5$, and then put in a 5% carbon dioxide ($CO_2$) incubator at 37° C. for culture.

6.2 After cell adhesion, the pEYFP-linker-Rluc and the pcDNA3.1-PLpro are transfected with a transfection reagent Lipofectamine 3000, and the sum of plasmids in each well is 900 nanograms (ng). After transfection, the experimental group is treated with different concentrations of RG-17 and GRL0617, and the drugs in the experimental group are diluted with DMSO. The final drug concentrations are set at 100 µM, 50 µM, 25 µM, 12.5 µM, 6.25 µM and 3.125 µM respectively, and the dosage volume is 10 µL. The control group is added with 10 µL DMSO. Then, they are cultured in a 5% $CO_2$ incubator at 37° C. for 48 h.

6.3 After 48 hours, the cells are washed twice with phosphate-buffered saline (PBS), digested and inoculated into a 96-well black opaque microplate (100 µL PBS/well), and triplicate wells are made in each group, and the number of cells in each well is set at $2\times10^4$.

6.4 The substrate conlenterazine of Rluc is added into the wells to the final concentration of 5 µM, and after 15 min at room temperature, the light intensities at 480 nm (±20 nm) and 535 nm (±10 nm) are measured with the microplate reader. In this situation, the BRET ratio is calculated, where:

$$BRET\ ratio = \frac{RLU_{EYEP}}{RLU_{Rluc}}.$$

In addition, the BRET ratios of the zero-setting group (also referred to as negative control group), the control group and the experimental group are analyzed, so as to determine the activity of PLpro. The groups are as follows:
the experimental group (293T cells transfected with the pEYFP-linker-Rluc plasmid and the pcDNA3.1-PLpro plasmid, containing PBS, conlenterazine, and the drug to be tested);
the control group (293T cells transfected with the pEYFP-linker-Rluc plasmid, containing PBS and conlenterazine, but without the drug to be tested); and
the negative control group (293T cells transfected with the pEYFP-linker-Rluc plasmid and the pcDNA3.1-PLpro plasmid, containing PBS and conlenterazine, without the drug to be tested).

$$Enzyme\ inhibition = \frac{BRET_{experimental\ group} - BRET_{negative\ control\ group}}{BRET_{control\ group} - BRET_{negative\ control\ group}}$$

6.5 Calculation of IC50: using GraphPad Prism software, with X as drug concentration and Y as enzyme inhibition, IC50 is analyzed and calculated. The results of in vivo enzyme assay shows that the IC50 of RG-17 is 13.66 µM, while that of GRL0617 as a control is 19.07 µM (FIGS. 7A-7D), so the inhibitory effect of RG-17 on PLpro is better than that of GRL0617.

Embodiment 7 Detection of Cytotoxicity of RG-17

The cytotoxicity of RG-17 and GRL0617 is detected by Cell Counting Kit-8 (CCK8) experiment, and the experimental steps are as follows.

7.1 Plating: A549 cells, MLE-12 cells and 293T cells in logarithmic growth phase are inoculated into 96-well plates (100 µL/well) respectively, and triplicate wells are made in each group, and the number of cells in each well is set at $5\times10^3$. The cells are put in a 5% $CO_2$ incubator at 37° C. for 12 h.

7.2 The experimental group is treated with different concentrations of RG-17 or GRL0617, and the drugs in the experimental group are diluted with DMSO. The dosage concentrations are set to 100 µM, 50 µM, 25 µM, 12.5 µM, 6.25 µM and 3.125 µM respectively, and the dosage volume is 2 µL. The control group is added with 2 µL DMSO. Then, they are put in a 5% $CO_2$ incubator at 37° C. for culture.

7.3 After 24 hours, the cells are washed with PBS twice, and then added 100 µL of pre-mixed CCK8 solution (medium: CCK8 working solution=9:1) to each well to avoid introduction of bubbles in the operation. Culture is continued for 2 h in a 5% $CO_2$ incubator at 37° C.

7.4 The absorbance $D(\lambda)$ of each well at the wavelength of 450 nm is determined by the microplate reader. $D(\lambda)$ values of the negative control group, the control group and the experimental group are analyzed to determine the cell activity. Cell viability reflects the cytotoxicity of the drug. The groups are as follows:
the experimental group (medium containing cells, CCK-8, the drug to be tested);
the control group (medium containing cells, CCK-8, without drug to be tested); and
the negative control group (medium without cells and the substance to be detected, with CCK-8).

$$Cell\ viability = \frac{D(\lambda)_{experimental\ group} - D(\lambda)_{negative\ control\ group}}{D(\lambda)_{control\ group} - D(\lambda)_{negative\ control\ group}}$$

Figure 8A:
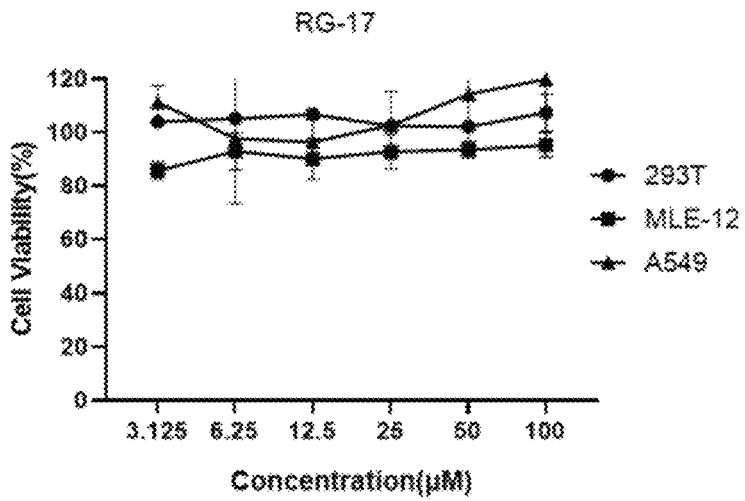
FIGS. 8A-8B illustrate cytotoxicity comparison between the RG-17 and the GRL0617.
Figure 8B:
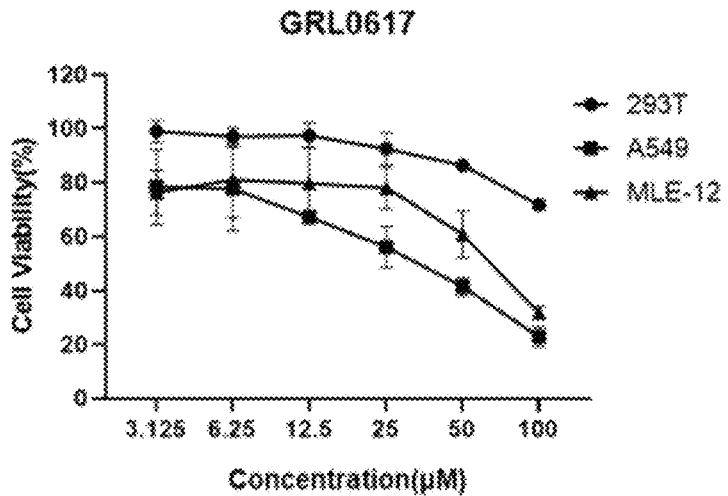

The results of CCK8 show that the cytotoxicity of RG-17 is much lower than that of GRL0617 at the same concentration, especially at high concentration (e.g., 100 µM, 50 µM), RG-17 does not affect the cell growth, while GRL0617 had great cytotoxicity (FIGS. 8A-8B).

Embodiment 8 the Polypeptide SRLRGG (SEQ ID NO: 1) is Linked with 6-TG to Obtain the Peptide-Drug Conjugate RG-6

Figure 9:
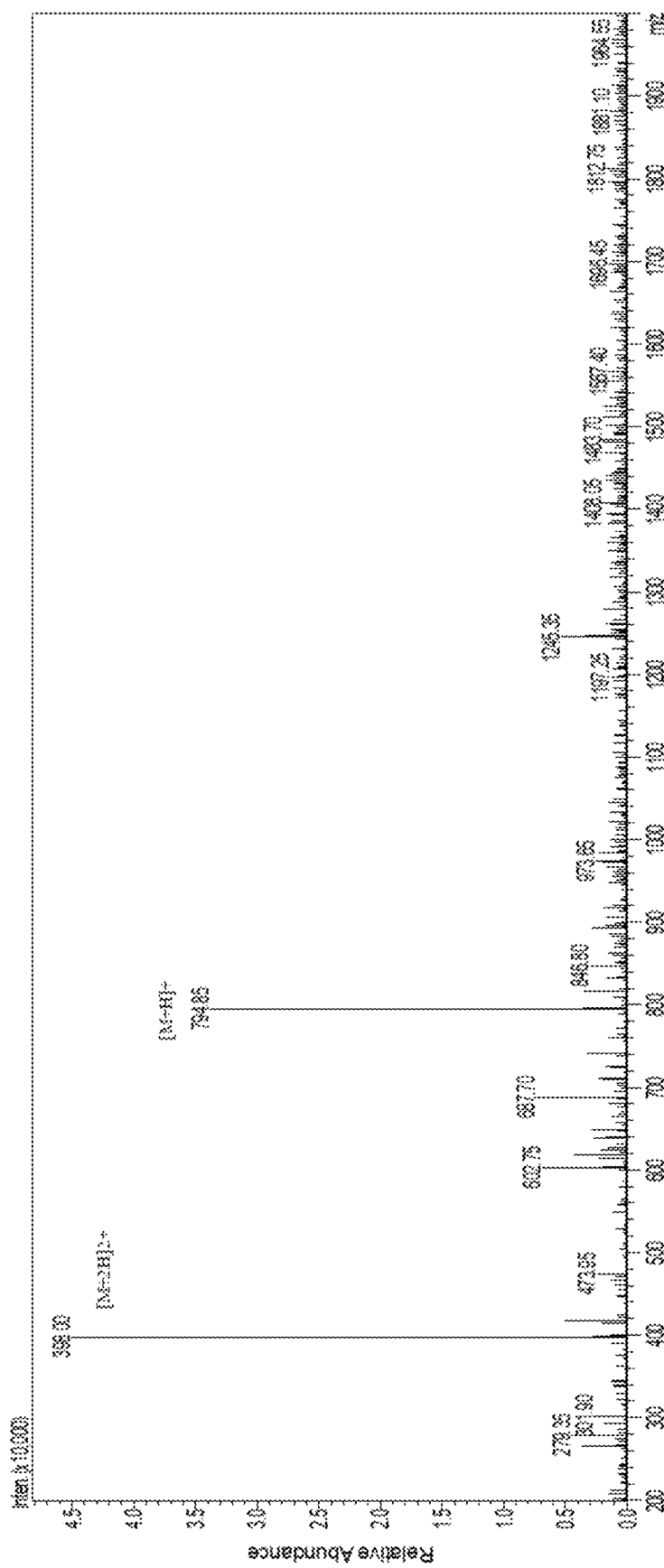
FIG. 9 illustrates a mass spectrum identification diagram of RG-6.
Figure 10:
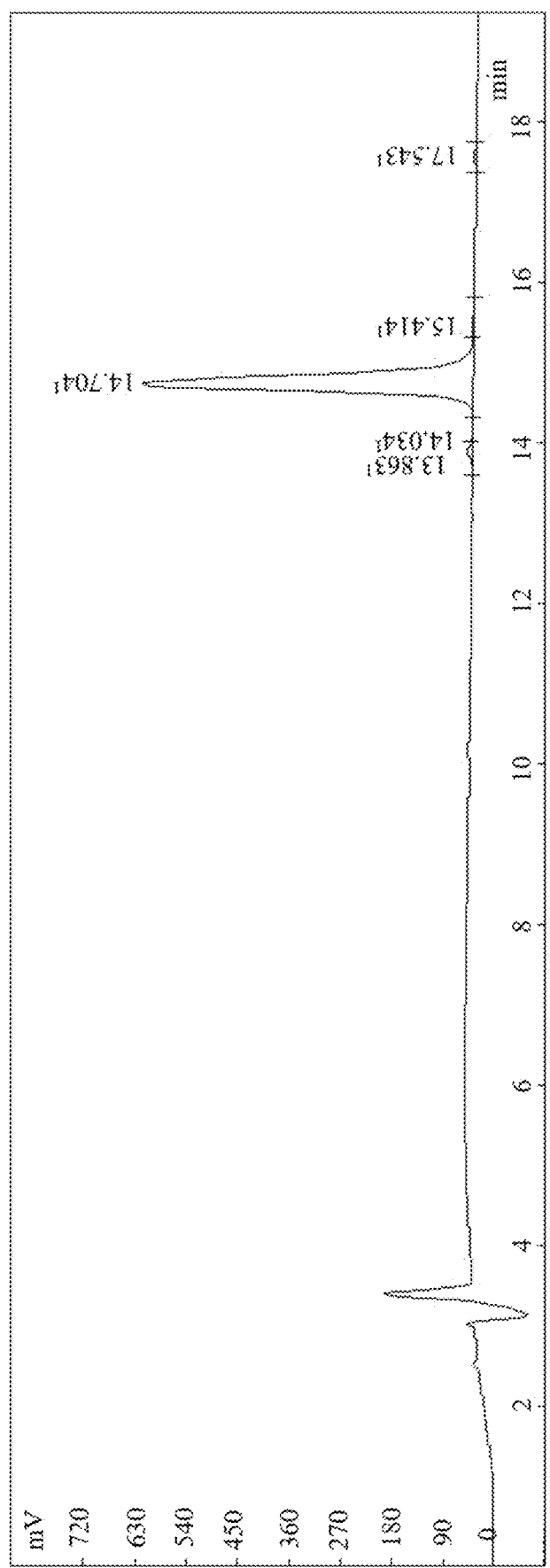
FIG. 10 illustrates an HPLC identification diagram of the RG-6.

The crude fully protected polypeptide obtained in the embodiment 2 is dissolved in 15 mL of anhydrous pyridine, and the temperature is reduced to −15° C. 1 mL $POCl_3$ solution to the solution is added, the anhydrous dichloromethane solution (1.5 equiv 6-TG) dissolved with 6-TG is gradually added dropwise at −15° C., reacted for 2 h, and a crude product is obtained after spin-drying. A cutting solution (95% TFA, 2% TIS; 2% EDT; 2% $H_2$) for 2 h, and a target product is obtained. It is confirmed by mass spectrometry (FIG. 9) and HPLC (FIG. 10) that the peptide-drug conjugate RG-6 formed by connecting the polypeptide SRLRGG (SEQ ID NO:1 and the 6-TG is successfully obtained. Its purity is more than or equal to 95%, and its structural formula is as follows:

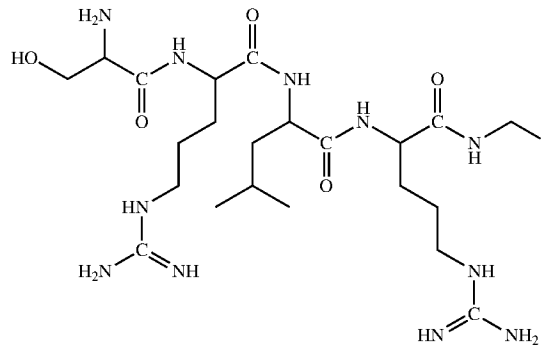

Embodiment 9 Detection of Cytotoxicity of RG-6

The cytotoxicity of RG-6 and 6-TG is detected by CCK8 experiment, and the experimental steps are as follows.

9.1 Plating: 293T cells in logarithmic growth phase are inoculated into a 96-well plate (100 μL/well), triplicate wells are made in each group, and the number of cells in each well is set at $5\times10^3$. The cells are put in a 5% $CO_2$ incubator at 37° C. for 12 h.

9.2 The experimental group is treated with different concentrations of RG-6 or 6-TG, and the drugs in the experimental group are diluted with DMSO. The dosage concentrations are set to 100 μM, 50 μM, 25 μM, 12.5 μM, 6.25 μM and 3.125 μM, and the dosage volume is 2 μL. The control group is added with 2 μL DMSO. Then, they are put in a 5% $CO_2$ incubator at 37° C. for culture.

9.3 After 24 hours, the cells are washed with PBS twice, and then added 100 μL of pre-mixed CCK8 solution (medium: CCK8 working solution=9:1) to each well to avoid introduction of bubbles in the operation. Culture is continued for 2 h in a 5 6% $CO_2$ incubator at 37° C.

9.4 The absorbance $D(\lambda)$ of each well at the wavelength of 450 nm is determined by the microplate reader. $D(\lambda)$ values of the negative control group, the control group and the experimental group are analyzed to determine the cell activity. Cell viability reflects the cytotoxicity of the drug. The groups are as follows:

the experimental group (medium containing cells, CCK-8, the drug to be tested);
the control group (medium containing cells, CCK-8, without drug to be tested); and
the negative control group (medium without cells and the substance to be detected, with CCK-8).

$$\text{Cell viability} = \frac{D(\lambda)_{experimental\ group} - D(\lambda)_{negative\ control\ group}}{D(\lambda)_{control\ group} - D(\lambda)_{negative\ control\ group}}$$

Figure 11:
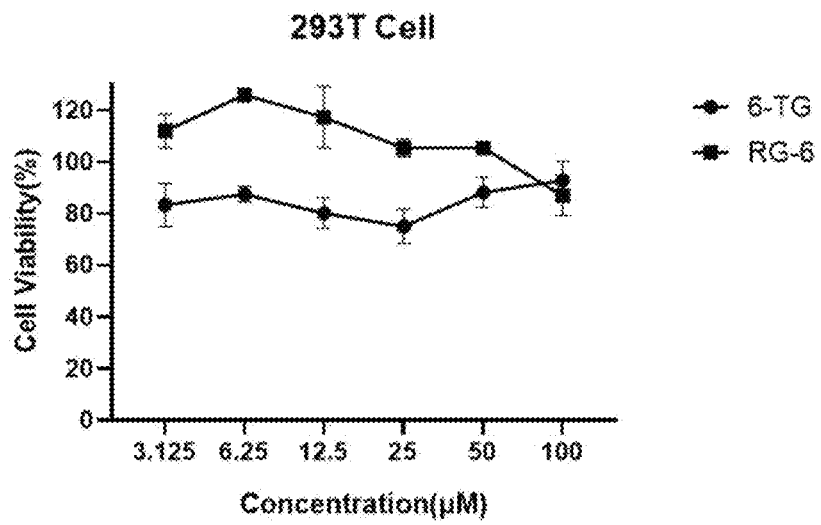
FIG. 11 illustrates cytotoxicity comparison between the RG-6 and the 6-TG.

The results of CCK8 show that the cells treated with RG-6 had higher activity than those treated with 6-TG at the same concentration, that is, RG-6 had less cytotoxicity than 6-TG (FIG. 11).

Embodiment 10 Test of the Inhibitory Effect of RG-17 and GRL0617 on SARS-CoV-2

The inhibitory effect of RG-17 and GRL0617 on SARS-CoV-2 is tested by using quantitative polymerase chain reaction (qPCR), and the specific steps are as follows.

10.1 Vero E6 cells are preserved in the virus room of the State Key Laboratory of Respiratory Diseases, Guangzhou Institute of Respiratory Health, China. Omicron BA5.2 variant of SARS-CoV-2 is isolated from throat swabs of patients in Guangzhou No. 8 People's Hospital of China, and preserved in Guangzhou Customs Technology Center P3 Laboratory (Highly Pathogenic Pathogen Microbiology Laboratory of the State Key Laboratory of Respiratory Disease) of China. The virus is cultured and amplified in the Vero E6 cells with Dulbecco's modified eagle's medium (DMEM) containing 2% fetal bovine serum.

10.2 A negative control (only virus is added to the medium without the drug) and a drug group (the virus and the drug are added to the medium) are set. Vero E6 cell suspension with a cell density of $2\times10^5$ cells/mL is spread in a sterile 24-well culture plate (500 μL is added to each well) and cultured at 37° C. and 5% $CO_2$ for 24 h.

10.3 The culture supernatant is discarded, 500 μL of SARS-CoV-2-containing medium (multiplicity of infection abbreviated as MOI=0.05) is added to each well, and the culture supernatant after routine culture adsorption for 2 h. 500 μL of new medium containing different concentrations of test drugs is added to each well, triplicate wells are made in each concentration, and the routine culture is carried out for 1 day.

10.4 The supernatant is removed from the medium, the cells are collected, the total RNA is extracted by Trizol method and reverse transcribed into complementary DNA (cDNA). The expression of nucleocapsid (N) gene of SARS-CoV-2 and glyceraldehyde 3-phosphate dehydrogenase (GAPDH) in cells are detected by qPCR, and the copy number of SARS-CoV-2 genome is calculated.

10.5 Calculation of IC50 by GraphPad Prism 8.0 software

Figure 12A:
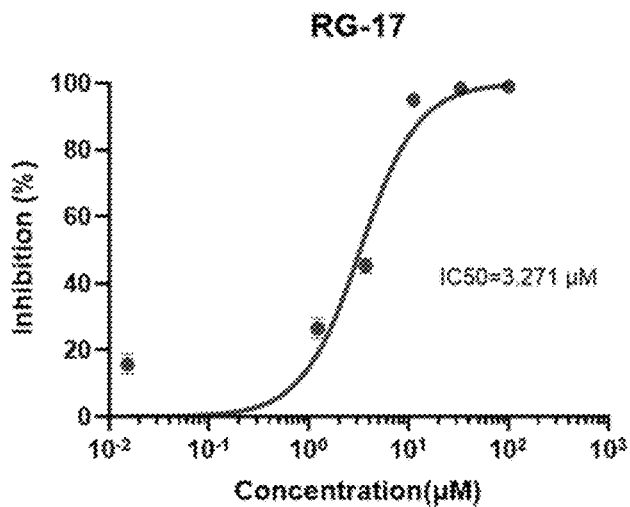
FIGS. 12A-12B illustrate inhibitory effects of the RG-17 and the GRL0617 on SARS-CoV-2.
Figure 12B:
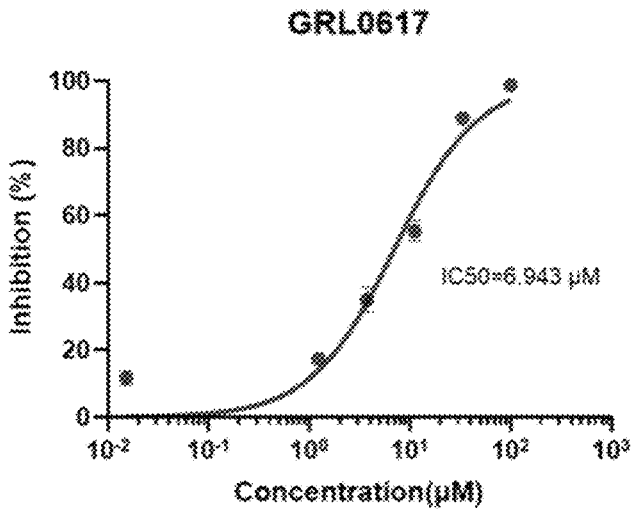

The results show (FIGS. 12A-12B) that RG-17 has better ability to inhibit the replication of the SARS-CoV-2 genome than GRL0617 without polypeptide coupling, and its IC50 is lower than GRL0617.

Embodiment 11 Test of the Inhibitory Effect of RG-6 and 6-TG on SARS-CoV-2

The inhibitory effect of RG-6 and 6-TG on SARS-CoV-2 is tested by cell plaque assay (reflecting the degree of virus amplification in cells), and the specific steps are as follows.

11.1 The sources of cells and SARS-CoV-2 are the same as in the embodiment 10. A cell control group (no virus or drug is added to the medium), a blank control group (DMSO solvent is added to the medium), a virus control group (only virus is added to the medium without drug), and a drug group (virus and drug are added to the culture medium) are set. Vero E6 cell suspension with a cell density of $2\times10^5$ cells/mL is spread in a sterile 96-well culture plate (100 μL is added to each well) and cultured at 37° C. and 5% $CO_2$ for 24 h.

11.2 The culture supernatant is discarded, 100 μL tissue culture infectious dose 50 ($TCID_{50}$) SARS-CoV-2 is added into each well of the drug group and the virus control group, and the culture supernatant is discarded after routine culture adsorption for 2 h. 100 μL of new medium containing different concentrations of test drugs is added to each well, triplicate wells are made in each concentration, and the routine culture is carried out for 3 days.

11.3 The cytopathic effect (CPE) is observed under the optical microscope, and the degrees of CPE are recorded according to the following 6-level criteria: "−" means that there is no CPE; "±" means that the CPE is less than 10%; "+" means that the CPE is about 25%; "++" means that the CPE is about 50%; "+++" means that the CPE is about 75%; and "++++" means that the CPE is more than 75%.

11.4 Calculation of IC50 by GraphPad Prism 8.0 software.

Figure 13A:
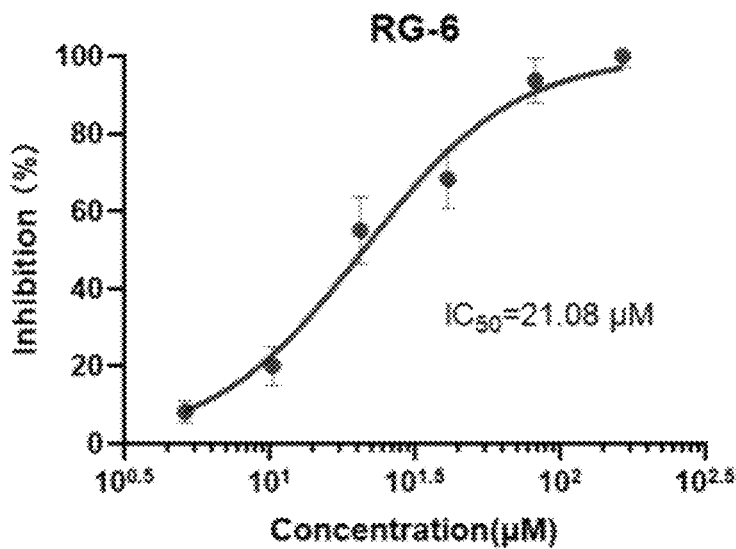
FIGS. 13A-13B illustrate inhibitory effects of the RG-6 and the 6-TG on the SARS-CoV-2.
Figure 13B:
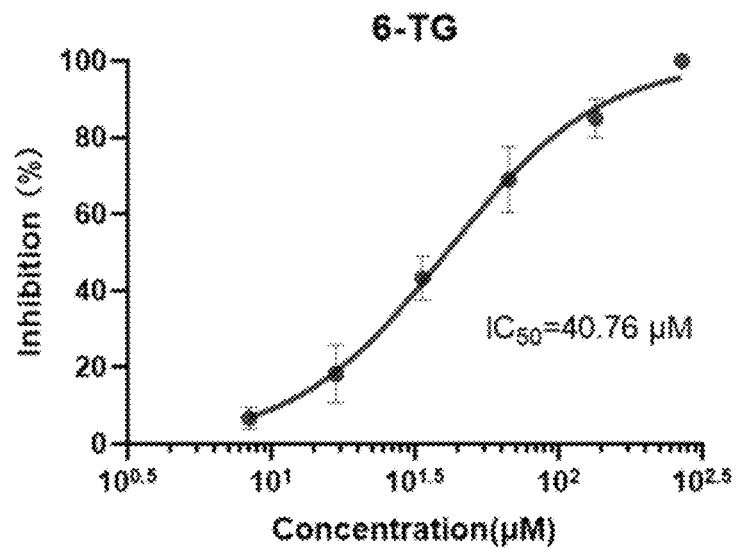

The results show (FIGS. 13A-13B) that RG-6 has better ability to inhibit the CPE induced by SARS-CoV-2 than 6-TG without polypeptide coupling, and its IC50 is lower than 6-TG.

The technical features of the above-mentioned embodiments can be combined arbitrarily. In order to make the description concise, not all possible combinations of the technical features in the above-mentioned embodiments are described. However, as long as there is no contradiction between the combinations of these technical features, they should be considered as the scope recorded in this specification.

The above-mentioned embodiments only illustrate several implementations of the disclosure, and their descriptions are more specific and detailed, but they cannot be understood as limiting the patent scope of the disclosure. It should be pointed out that for those skilled in the art, without departing from the concept of the disclosure, a number of variations and improvements can be made, which are within the scope of protection of the disclosure. Therefore, the scope of protection of the patent of this disclosure should be subject to the appended claims.

SEQUENCE LISTING

```
Sequence total quantity: 6
SEQ ID NO: 1              moltype = AA   length = 6
FEATURE                   Location/Qualifiers
source                    1..6
                          mol_type = protein
                          organism = synthetic construct
SEQUENCE: 1
SRLRGG                                                                      6

SEQ ID NO: 2              moltype = DNA  length = 5543
FEATURE                   Location/Qualifiers
source                    1..5543
                          mol_type = other DNA
                          organism = synthetic construct
SEQUENCE: 2
tagttattaa tagtaatcaa ttacggggtc attagttcat agcccatata tggagttccg   60
cgttacataa cttacggtaa atggcccgcc tggctgaccg cccaacgacc cccgcccatt  120
gacgtcaata atgacgtatg ttcccatagt aacgccaata gggactttcc attgacgtca  180
atgggtggag tatttacggt aaactgccca cttggcagta catcaagtgt atcatatgcc  240
aagtacgccc cctattgacg tcaatgacgg taaatggccc gcctggcatt atgcccagta  300
catgacctta tgggactttc ctacttggca gtacatctac gtattagtca tcgctattac  360
catggtgatg cggttttggc agtacatcaa tgggcgtgga tagcggtttg actcacgggg  420
atttccaagt ctccacccca ttgacgtcaa tgggagtttg ttttggcacc aaaatcaacg  480
ggactttcca aaatgtcgta acaactccgc cccattgacg caaatgggcg gtaggcgtgt  540
acggtgggag gtctatataa gcagagctgg tttagtgaac cgtcagatcc gctagcgcta  600
ccggactcag atctcgagat ggtgagcaag ggcgaggagc tgttcaccgg ggtggtgccc  660
atcctggtcg agctggacgg cgacgtaaac ggccacaagt tcagcgtgtc cggcgagggc  720
gagggcgatg ccacctacgg caagctgacc ctgaagttca tctgcaccac cggcaagctg  780
cccgtgccct ggcccaccct cgtgaccacc ttcggctacg gcctgcagtg cttcgcccgc  840
taccccgacc acatgaagca gcacgacttc ttcaagtccg ccatgcccga aggctacgtc  900
caggagcgca ccatcttctt caaggacgac ggcaactaca agacccgcgc cgaggtgaag  960
ttcgagggcg acaccctggt gaaccgcatc gagctgaagg gcatcgactt caaggaggac 1020
ggcaacatcc tggggcacaa gctggagtac aactacaaca gccacaacgt ctatatcatg 1080
gccgacaagc agaagaacgg catcaaggtg aacttcaaga tccgccacaa catcgaggac 1140
ggcagcgtgc agctcgccga ccactaccag cagaacaccc ccatcggcga cggccccgtg 1200
ctgctgcccg acaaccacta cctgagctac cagtccgccc tgagcaaaga ccccaacgag 1260
aagcgcgatc acatggtcct gctggagttc gtgaccgccg ccgggatcac tctcggcatg 1320
gacgagctgt acaaggagct cataacctcg agactgagag gcggcttcag aaagggatcc 1380
atgacttcga aagtttatga tccagaacaa aggaaacgga tgataactgg tccgcagtgg 1440
tgggccagat gtaaacaaat gaatgttctt gattcattta ttaattatta tgattcagaa 1500
aaacatgcag aaaatgctgt tattttttta catggtaacg cggcctcttc ttatttatgg 1560
cgacatgttg tgccacatat tgagccagta gcgcggtgta ttataccaga cctattggt  1620
atgggcaaat caggcaaatc tggtaatggt tcttataggt tacttgatca ttacaaatat 1680
cttactgcat ggtttgaact tcttaattta ccaaagaaga tcatttttgt cggccatgat 1740
tggggtgctg ctttggcatt tcattatagc tatgagcatc aagataagat caaagcaata 1800
gttcacgctg aaagtgtagt agatgtgatt gaatcatggg atgaatggcc tgatattgaa 1860
```

```
gaagatattg cgttgatcaa atctgaagaa ggagaaaaaa tggttttgga gaataacttc  1920
ttcgtggaaa ccatgttgcc atcaaaaatc atgagaaagt tagaaccaga agaatttgca  1980
gcatatcttg aaccattcaa agagaaaggt gaagttcgtc gtccaacatt atcatggcct  2040
cgtgaaatcc cgttagtaaa aggtggtaaa cctgacgttg tacaaattgt taggaattat  2100
aatgcttatc tacgtgcaag tgatgattta ccaaaaatgt ttattgaatc ggacccagga  2160
ttcttttcca atgctattgt tgaaggtgcc aagaagtttc ctaatactga atttgtcaaa  2220
gtaaaaggtc ttcattttc gcaagaagat gcacctgatg aaatgggaaa atatatcaaa  2280
tcgttcgttg agcgagttct caaaaatgaa caataacaat tgttgttgtt aacttgttta  2340
ttgcagctta taatggttac aaataaagca atagcatcac aaatttcaca aataaagcat  2400
tttttcact gcattctagt tgtggtttgt ccaaactcat caatgtatct taaggcgtaa  2460
attgtaagcg ttaatatttt gttaaaattc gcgttaaatt tttgttaaat cagctcattt  2520
tttaaccaat aggccgaaat cggcaaaatc ccttataaat caaagaata gaccgagata  2580
gggttgagtg ttgttccagt ttggaacaag agtccactat taaagaacgt ggactccaac  2640
gtcaaagggc gaaaaaccgt ctatcagggc gatggcccac tacgtgaacc atcaccctaa  2700
tcaagttttt tggggtcgag gtgccgtaaa gcactaaatc ggaacctaa agggagcccc  2760
cgatttagag cttgacgggg aaagccggcg aacgtggcga aaaggaagg gaagaaagcg  2820
aaaggagcgg gcgctagggc gctggcaagt gtagcggtca cgctgcgcgt aaccaccaca  2880
cccgccgcgc ttaatgcgcc gctacagggc gcgtcaggtg gcacttttcg gggaaatgtg  2940
cgcggaaccc ctatttgttt attttctaa atacattcaa atatgtatcc gctcatgaga  3000
caataaccct gataaatgct tcaataatat tgaaaagga agagtcctga ggcggaaaga  3060
accagctgtg aatgtgtgt cagttagggt gtggaaagtc cccaggctcc ccagcaggca  3120
gaagtatgca aagcatgcat ctcaattagt cagcaaccag gtgtggaaag tccccaggct  3180
ccccagcagg cagaagtatg caaagcatgc atctcaatta gtcagcaacc atagtcccgc  3240
ccctaactcc gcccatcccg ccctaactc gcccagttc gcccattct ccgcccatg  3300
gctgactaat ttttttatt tatgcagagg ccgaggccgc ctcggcctct gagctattcc  3360
agaagtagtg aggaggcttt tttggaggcc taggcttttg caaagatcga tcaagagaca  3420
ggatgaggat cgtttcgcat gattgaacaa gatggattgc acgcaggttc tccggccgct  3480
tgggtggaga ggctattcgg ctatgactgg gcacaacaga caatcggctg ctctgatgcc  3540
gccgtgttcc ggctgtcagc gcaggggcgc ccggttcttt ttgtcaagac cgacctgtcc  3600
ggtgccctga atgaactgca agacgaggca gcgcggctat cgtggctggc cacgacgggc  3660
gttccttgcg cagctgtgct cgacgttgtc actgaagcgg gaagggactg gctgctattg  3720
ggcgaagtgc cggggcagga tctcctgtca tctcaccttg ctcctgccga gaaagtatcc  3780
atcatggctg atgcaatgcg gcggctgcat acgcttgatc cggctacctg cccattcgac  3840
caccaagcga aacatcgcat cgagcgagca cgtactcgga tggaagccgg tcttgtcgat  3900
caggatgatc tggacgaaga gcatcagggg ctcgcgccag ccgaactgtt cgccaggctc  3960
aaggcgagca tgcccgacgg cgaggatctc gtcgtgaccc atggcgatgc ctgcttgccg  4020
aatatcatgg tggaaaatgg ccgcttttct ggattcatcg actgtggccg gctgggtgtg  4080
gcggaccgct atcaggacat agcgttggct acccgtgata ttgctgaaga gcttggcggc  4140
gaatgggctg accgcttcct cgtgctttac ggtatcgccg ctcccgattc gcagcgcatc  4200
gccttctatc gccttcttga cgagttcttc tgagcgggac tctggggttc gaaatgaccg  4260
accaagcgac gcccaacctg ccatcacgag atttcgattc caccgccgcc ttctatgaaa  4320
ggttgggctt cggaatcgtt ttccgggacg ccggctggat gatcctccag cgcggggatc  4380
tcatgctgga gttcttcgcc cacccctaggg gaggctaac tgaaacacgg aaggagacaa  4440
taccggaagg aacccgcgct atgacgcgaa taaaaagaca gaataaaacg cacggtgttg  4500
ggtcgtttgt tcataaacgc ggggttcggt cccaggctg gcactctgtc gatccccac  4560
cgagacccca ttggggccaa tacgcccgcg tttcttcctt ttccccaccc cacccccaa  4620
gttccggtga aggccaggg ctcgcagcca acgtcgggc gcaggccct gccatagcct  4680
caggttactc atatatactt tagattgatt taaaacttca ttttaatttt aaaaggatct  4740
aggtgaagat ccttttttgat aatctcatga ccaaaatccc ttaacgtgag ttttcgttcc  4800
actgagcgtc agacccgta gaaagatca aggatcttc ttgagatcct ttttttctgc  4860
gcgtaatctg ctgcttgcaa acaaaaaaac caccgctacc agcggtggtt tgtttgcgga  4920
atcaagagct accaactctt tttccgaagg taactggctt cagcagagcg cagataccaa  4980
atactgtcct tctagtgtag ccgtagttag gccaccactt caagaactct gtagcaccgc  5040
ctacatacct cgctctgcta atcctgttac cagtggctgc tgccagtggc gataagtcgt  5100
gtcttaccgg gttggactca agacgatagt taccggataa ggcgcagcgg tcgggctgaa  5160
cggggggttc gtgcacacag cccagcttgg agcgaacgac ctacaccgaa ctgagatacc  5220
tacagcgtga gctatgagaa agcgccacgc ttcccgaagg gagaaaggcg gacaggtatc  5280
cggtaagcgg cagggtcgga acaggagagc gcacgaggga gcttccaggg ggaaacgcct  5340
ggtatcttta tagtcctgtc gggtttcgcc acctctgact tgagcgtcga tttttgtgat  5400
gctcgtcagg gggcggagc ctatggaaaa acgccagcaa cgcggccttt ttacggttcc  5460
tggccttttg ctggcctttt gctcacatgt tctttcctgc gttatcccct gattctgtgg  5520
ataaccgtat taccgccatg cat                                         5543
```

SEQ ID NO: 3          moltype = AA   length = 11
FEATURE               Location/Qualifiers
source                1..11
                      mol_type = protein
                      organism = synthetic construct
SEQUENCE: 3
ITSRLRGGFR K                                                         11

SEQ ID NO: 4          moltype = DNA   length = 7009
FEATURE               Location/Qualifiers
source                1..7009
                      mol_type = other DNA
                      organism = synthetic construct
SEQUENCE: 4
```
gacggatcgg gagatctccc gatcccctat ggtgcactct cagtacaatc tgctctgatg   60
ccgcatagtt aagccagtat ctgctccctg cttgtgtgtt ggaggtcgct gagtagtgcg  120
```

```
cgagcaaaat ttaagctaca acaaggcaag gcttgaccga caattgcatg aagaatctgc   180
ttagggttag gcgttttgcg ctgcttcgcg agtacattta tattggctca tgtccaatat   240
gaccgccatg ttgacattga ttattgacta gttattaata gtaatcaatt acggggtcat   300
tagttcatag cccatatatg gagttccgcg ttacataact tacggtaaat ggcccgcctg   360
gctgaccgcc caacgacccc cgcccattga cgtcaataat gacgtatgtt cccatagtaa   420
cgccaatagg gactttccat tgacgtcaat gggtggagta tttacggtaa actgcccact   480
tggcagtaca tcaagtgtat catatgccaa gtccgcccc tattgacgtc aatgacggta    540
aatgccccgc ctggcattat gcccagtaca tgaccttacg ggactttcct acttggcagt   600
acatctacgt attagtcatc gctattacca tggtgatgcg gttttggcag tacaccaatg   660
ggcgtggata gcggtttgac tcacggggat ttccaagtct ccaccccatt gacgtcaatg   720
ggagtttgtt ttggcaccaa aatcaacggg actttccaaa atgtcgtaat aaccccgccc   780
cgttgacgca aatgggcggt aggcgtgtac ggtgggaggt ctatataagc agagctcgtt   840
tagtgaaccg tcagatcctc actctcttcc gcatcgctgt ctgcgagggc cagctgttgg   900
gctcgcggtt gaggacaaac tcttcgcggt ctttccagta ctcttggatc ggaaacccgt   960
cggcctccga acggtactcc gccaccgagg gacctgagcg agtccgcatc gaccggatcg  1020
gaaaacctct cgagaaaggc gtctaaccag tcacagtcgc aaggtaggct gagcaccgtg  1080
gcgggcggca gcgggtggcg gtcggggttg tttctggcgg aggtgctgct gatgatgtaa  1140
ttaaagtagg cggtcttgag acggcgggatg gtcgaggtga ggtgtggcag gcttgagatc  1200
cagctgttgg ggtgagtact ccctctcaaa agcgggcatt acttctgcgc taagattgtc  1260
agtttccaaa aacgaggagg attttgatatt cacctggccc gatctggcca tacacttgag  1320
tgacaatgac atccactttg cctttctctc cacaggtgtc cactcccagg tccaagttta  1380
aactttaata cgactcacta taggggccgc caccaagctt ggtaccatgg aagtgaggac  1440
tattaaggtg tttacaacag tagacaacat taacctccac acgcaagttg tggacatgtc  1500
aatgacatat ggacaacagt ttggtccaac ttatttggat ggagctgatg ttactaaaat  1560
aaaacctcat aattcacatg aaggtaaaac atttatgtt ttacctaatg atgacactct   1620
acgtgttgag gcttttgagt actaccacac aactgatcct agttttctgg gtaggtacat  1680
gtcagcatta aatcacacta aaagtggaaa atacccacaa gttaatggtt taacttctat  1740
taaatgggca gataacaact gttatcttgc cactgcattg ttaacactcc aacaaatagaa 1800
gttgaagttt aatccacctg ctctacaaga tgcttattac agagcaaggg ctggtgaagc  1860
tgctaacttt tgtgccatta tcttagccta ctgtaataag acagtaggtg agttaggtga  1920
tgttagagaa acaatgagtt acttgttcca acatgccaat ttagattctt gcaaaagagt  1980
cttgaacgtg gtgtgtaaaa cttgtggaca acagcagaca ccccttaagg gtgtagaagc  2040
tgttatgtac atgggcacac tttcttatga acaatttaag aaaggtgttc agataccttg  2100
tacgtgtggt aaacaagcta caaaatatct agtacaacag gagtccactt ttgttatgat  2160
gtcagcacca cctgctcagt atgaacttaa gcatgataca tttacttgtg ctagtgagta  2220
cactggtaat taccagtgtg gtcactataa acatataact tctaaagaaa ctttgtattg  2280
catagacggt gctttactta caaagtcctc agaatacaaa ggtcctatta cggatgtttt  2340
ctacaaagaa aacagttaca caacaacat aaaaccagtt tgaatctaga gcggccgcg   2400
aattaacgc cgtttaaacc cgctgatcag cctcgactgt gccttctagt tgccagccat  2460
ctgttgtttg ccctccccc gtgccttcct tgacccctgga aggtgccact cccactgtcc  2520
tttcctaata aaatgaggaa attgcatcgc attgtctgag taggtgtcat tctattctgg  2580
ggggtgggt ggggcaggac agcaagggggg aggattggga agacaatagc aggcatgctg   2640
gggatgcggt gggctctatg gcttctgagg cggaaagaac cagctggggc tctagggggt  2700
atcccccacgc gccctgtagc ggcgcattaa gcgcggcggg tgtggtggtt acgcgcagcg  2760
tgaccgctac acttgccagc gccctagcgc ccgctccttt cgctttcttc ccttcctttc  2820
tcgccacgtt cgccggcttt ccccgtcaag ctctaaatcg gggctccct ttagggttcc    2880
gatttagtgc tttacggcac ctcgaccca aaaaacttga ttagggtgat ggttcacgta   2940
gtgggccatc gccctgatag acggttttc gccctttgac gttggagtcc acgttcttta   3000
atagtggact cttgttccaa actggaacaa cactcaaccc tatctcggtc tattcttttg  3060
atttataagg gattttgccg atttcggcct attggttaaa aaatgagctg atttaacaaa  3120
aatttaacgc gaattaattc tgtggaatgt gtgtcagtta gggtgtggaa agtccccagg  3180
ctccccagca ggcagaagta tgcaaagcat gcatctcaat tagtcagcaa ccaggtgtgg  3240
aaagtcccca ggctccccag caggcagaag tatgcaaagc atgcatctca attagtcagc  3300
aaccatagtc ccgcccctaa ctccgcccat cccgcccta actccgccca gttccgccca  3360
ttctccgccc catggctgac taatttttt tatttatgca gaggccgagg ccgcctctgc  3420
ctctgagcta ttccagaagt agtgaggagg ctttttttgga ggcctaggct tttgcaaaaa  3480
gctcccggga gcttgtatat ccattttcgg atctgatcag cacgtgatga aaagcctga   3540
actcaccgcg acgtctgtcg agaagtttct gatcgaaaag ttcgacagcg tctccgacct  3600
gatgcagctc tcggagggcg aagaatctcg tgctttcagc ttcgatgtag gagggcgtgg  3660
atatgtcctg cgggtaaata gctgcgccga tggtttctac aaagatcgtt atgtttatcg  3720
gcactttgca tcggccgcgc tcccgattcc ggaagtgctt gacattgggg aattcagcga  3780
gagcctgacc tattgcatct cccgccgtgc acagggtgtc acgttgcaag acctgcctga  3840
aaccgaactg cccgctgttc tgcagccggt cgcggaggcc atggatgcga tcgctgcggc  3900
cgatcttagc cagacgagcg gttcggccc attggaacg caaggaatcg tcaatacac    3960
tacatggcgt gatttcatat gcgcgattgc tgatccccat gtgtatcact ggcaaactgt  4020
gatgacgac accgtcagtg cgtccgtcgc gcaggctctc gatgagctga tgctttgggc  4080
cgaggactgc cccgaagtcc ggcacctcgt gcacgcggat ttcggctcca acaatgtcct  4140
gacggacaat ggccgcataa cagcggtcat tgactggagc gaggcgatgt tcggggattc  4200
ccaatacgag gtcgccaaca tcttcttctg gaggccggtt ggcttgtta ggagcagcaa   4260
gacgcgctac ttcgagcgga ggcatccgga gcttgcagga tcgccgcggc tccgggcgta  4320
tatgctccgc attggtcttg accaactcta tcagagcttg gttgacggca atttcgatga  4380
tgcagcttgg gcgcagggtc gatgcgacgc aatcgtccga tccggagccg gactgtcgg   4440
gcgtacacaa atcgcccgca gaagcgcggc cgtctggacc gatggctgtg tagaagtact  4500
cgccgatagt ggaaaccgac gccccagcac tcgtccgagg caaaggaat agcacgtgct  4560
acgagatttc gattcaccg ccgccttcta tgaaaggttg gcttcggaa tcgttttccg   4620
ggacgccggc tggatgatcc tccagcgcgg ggatctcatg ctggagttct tcgcccaccc  4680
caacttgttt attgcagctt ataatggtta caaataaagc aatagcatca caaatttcac  4740
aaataaagca tttttttcac tgcattctag ttgtggtttg tccaaactca tcaatgtatc  4800
ttatcatgtc tgtataccgt cgacctctag ctagagcttg gcgtaatcat ggtcatagct  4860
```

```
gtttcctgtg tgaaattgtt atccgctcac aattccacac aacatacgag ccggaagcat   4920
aaagtgtaaa gcctggggtg cctaatgagt gagctaactc acattaattg cgttgcgctc   4980
actgcccgct ttccagtcgg gaaacctgtc gtgccagctg cattaatgaa tcggccaacg   5040
cgcggggaga ggcggtttgc gtattgggcg ctcttccgct tcctcgctca ctgactcgct   5100
gcgctcggtc gttcggctgc ggcgagcggt atcagctcac tcaaaggcgg taatacggtt   5160
atccacagaa tcaggggata acgcaggaaa gaacatgtga gcaaaaggcc agcaaaaggc   5220
caggaaccgt aaaaaggccg cgttgctggc gtttttccat aggctccgcc ccctgacga    5280
gcatcacaaa aatcgacgct caagtcagag gtggcgaaac ccgacaggac tataaagata   5340
ccaggcgttt cccctggaa  gctccctcgt gcgctctcct gttccgaccc tgccgcttac    5400
cggatacctg tccgcctttc tcccttcggg aagcgtggcg ctttctcata gctcacgctg   5460
taggtatctc agttcggtgt aggtcgttcg ctccaagctg ggctgtgtgc acgaaccccc   5520
cgttcagccc gaccgctgcg ccttatccgg taactatcgt cttgagtcca cccggtaag    5580
acacgactta tcgccactgg cagcagccac tggtaacagg attagcagag cgaggtatgt   5640
aggcggtgct acagagttct tgaagtggtg gcctaactac ggctacacta gaagaacagt   5700
atttggtatc tgcgctctgc tgaagccagt taccttcgga aaaagagttg gtagctcttg   5760
atccggcaaa caaccaccg  ctggtagcgg tggttttttt gtttgcaagc agcagattac    5820
gcgcagaaaa aaaggatctc aagaagatcc tttgatcttt tctacggggt ctgacgctca   5880
gtggaacgaa aactcacgtt aagggatttt ggtcatgaga ttatcaaaaa ggatcttcac   5940
ctagatcctt ttaaattaaa aatgaagttt taaatcaatc taaagtatat atgagtaaac   6000
ttggtctgac agttaccaat gcttaatcag tgaggcacct atctcagcga tctgtctatt   6060
tcgttcatcc atagttgcct gactcccgt  cgtgtagata actacgatac gggagggctt    6120
accatctggc cccagtgctg caatgatacc gcgagaccca cgctcaccgg ctccagattt   6180
atcagcaata aaccagccag ccggaagggc cgagcgcaga agtggtcctg caactttatc   6240
cgcctccatc cagtctatta attgttgccg ggaagctaga gtaagtagtt cgccagttaa   6300
tagtttgcgc aacgttgttg ccattgctac aggcatcgtg gtgtcacgct cgtcgtttgg   6360
tatggcttca ttcagctccg gttcccaacg atcaaggcga gttacatgat ccccccatgtt  6420
gtgcaaaaaa gcggttagct ccttcggtcc tccgatcgtt gtcagaagta agttggccgc   6480
agtgttatca ctcatggtta tggcagcact gcataattct cttactgtca tgccatccgt   6540
aagatgcttt tctgtgactg gtgagtactc aaccaagtca ttctgagaat agtgtatgcg   6600
gcgaccgagt tgctcttgcc cggcgtcaat acgggataat accgcgccac atagcagaac   6660
tttaaaagtg ctcatcattg gaaaacgttc ttcggggcga aaactctcaa ggatcttacc   6720
gctgttgaga tccagttcga tgtaaccac  tcgtgcaccc aactgatctt cagcatcttt    6780
tactttcacc agcgtttctg ggtgagcaaa aacaggaagg caaaatgccg caaaaaaggg   6840
aataagggcg acacggaaat gttgaatact catactcttc cttttttcaat attattgaag  6900
catttatcag ggttattgtc tcatgagcgg atacatattt gaatgtattt agaaaaataa   6960
acaaataggg gttccgcgca catttccccg aaaagtgcca cctgacgtc                7009
```

| | | |
|---|---|---|
| SEQ ID NO: 5 | moltype = AA   length = 6 | |
| FEATURE | Location/Qualifiers | |
| source | 1..6 | |
| | mol_type = protein | |
| | organism = synthetic construct | |
| BINDING | | |
| | note = tert-butyloxycarbonyl (Boc) | |
| MOD_RES | 1 | |
| | note = tert-butyl (Tbu) | |
| MOD_RES | 2 | |
| | note = 4-(2,2,2-trifluoroethoxy)phenyl (pbf) | |
| MOD_RES | 4 | |
| | note = 4-(2,2,2-trifluoroethoxy)phenyl (pbf) | |
| SEQUENCE: 5 | | |
| SRLRGG | | 6 |
| | | |
| SEQ ID NO: 6 | moltype = AA   length = 6 | |
| FEATURE | Location/Qualifiers | |
| source | 1..6 | |
| | mol_type = protein | |
| | organism = synthetic construct | |
| BINDING | 6 | |
| | note = 7-amino-4-methylcoumarin (AMC) | |
| SEQUENCE: 6 | | |
| SRLRGG | | 6 |

What is claimed is:

1. A peptide-coupled molecule compound, wherein the peptide comprises the amino acid sequence SRLRGG (SEQ ID NO: 1);
the molecule compound inhibits a coronavirus papain-like protease (PLpro) activity; and
wherein the C-terminal carboxyl group of the peptide and the molecule compound are chemically bound by an amide bond or an ester bond.

2. The peptide-coupled molecule compound of claim 1, wherein the molecule compound is GRL0617.

3. The peptide-coupled molecule compound of claim 2, comprising the following structure

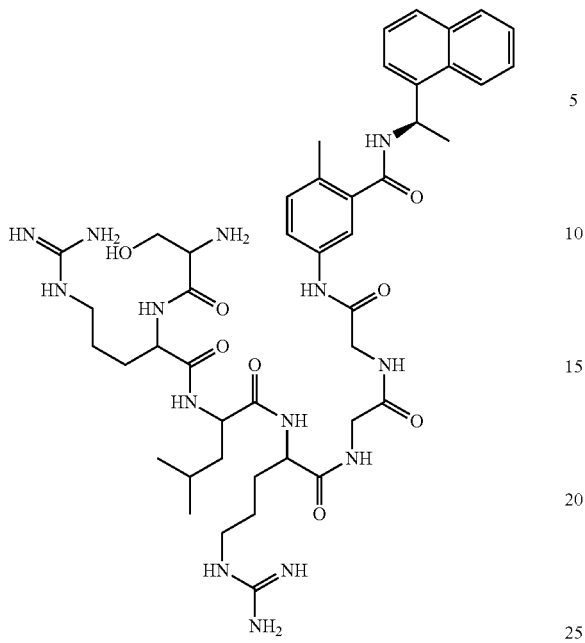

4. The peptide-coupled molecule compound of claim 1, wherein the molecule compound is 6-thioguanine.

5. The peptide-coupled molecule compound of claim 4, wherein the peptide-coupled molecule compound comprises the structure

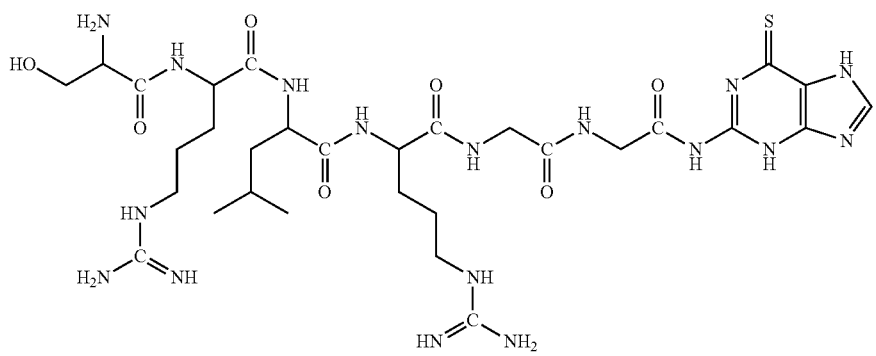 [SMILES: CC(C)CC(NC(=O)C(CCCNC(=N)N)NC(=O)C(N)CO)C(=O)NC(CCCNC(=N)N)C(=O)NCC(=O)NCC(=O)Nc1nc(=S)c2[nH]cnc2[nH]1]

6. The peptide-coupled molecule compound of claim 1, wherein the molecule compound is levothyroxine.

7. The peptide-coupled molecule compound of claim 1, wherein the molecule compound is loperamide.

8. The peptide-coupled molecule compound of claim 1, wherein the molecule compound is proanthocyanidin.

9. An anti-coronavirus drug comprising the peptide-coupled molecule compound of claim 1 and a pharmaceutically acceptable excipient.

\* \* \* \* \*